United States Patent
Seedhom et al.

(10) Patent No.: US 11,259,810 B2
(45) Date of Patent: Mar. 1, 2022

(54) DEVICE, ASSEMBLY AND METHOD FOR USE IN TENDON REPAIR

(71) Applicant: Xiros Limited, Leeds (GB)

(72) Inventors: Bahaa Botros Seedhom, Leeds (GB); Corey James Robinson, Leeds (GB)

(73) Assignee: Xiros Limited, Leeds (GB)

( * ) Notice: Subject to any disclaimer, the term of this patent is extended or adjusted under 35 U.S.C. 154(b) by 137 days.

(21) Appl. No.: 16/401,929

(22) Filed: May 2, 2019

(65) Prior Publication Data
US 2019/0380713 A1 Dec. 19, 2019

(30) Foreign Application Priority Data

| Jun. 18, 2018 | (GB) | 1809949 |
| Dec. 19, 2018 | (GB) | 1820699 |
| Jan. 31, 2019 | (GB) | 1901357 |

(51) Int. Cl.
*A61B 17/11* (2006.01)
*A61B 17/04* (2006.01)
(Continued)

(52) U.S. Cl.
CPC ...... *A61B 17/1146* (2013.01); *A61B 17/0482* (2013.01); *A61B 2017/00862* (2013.01);
(Continued)

(58) Field of Classification Search
CPC ........ A61B 17/1146; A61B 2017/1132; A61B 17/0482; A61B 2017/1107;
(Continued)

(56) References Cited

U.S. PATENT DOCUMENTS

| 5,236,443 A | 8/1993 | Sontag |
| 5,549,629 A | 8/1996 | Thomas et al. |

(Continued)

FOREIGN PATENT DOCUMENTS

| CN | 205569148 U | 9/2016 |
| CN | 10603 8018 A | 10/2016 |

(Continued)

OTHER PUBLICATIONS

Communication Relating to the Results of the Partial International Search of the International Searching Authority, dated Aug. 29, 2019, for corresponding International Application No. PCT/GB2019/051686, 18 pages.

(Continued)

*Primary Examiner* — Darwin P Erezo
*Assistant Examiner* — Brigid K Byrd
(74) *Attorney, Agent, or Firm* — Klarquist Sparkman, LLP

(57) ABSTRACT

An assembly for use in repairing a severed tendon comprises an elongate threading element adapted to transit along a lumen of a tendon sheath, for covering a curved needle and carrying the needle within the lumen. The assembly can also comprise a liner for lining an internal surface of the tendon sheath, defining an internal passage along which a tendon stump coupled to the curved needle can pass. The liner can have a collapsed, rest configuration in which it is adapted to be inserted into the lumen of the tendon sheath, and an expanded, operating configuration, the liner being movable to the expanded configuration by contact with the tendon stump. Once released from the liner, the threading element receives the curved needle, for covering and carrying the curved needle through the liner and along the lumen of the tendon sheath trailing the connected tendon stump.

38 Claims, 19 Drawing Sheets

(51) Int. Cl.
*A61B 17/00* (2006.01)
*A61B 17/06* (2006.01)

(52) U.S. Cl.
CPC ............... *A61B 2017/0608* (2013.01); *A61B 2017/1132* (2013.01)

(58) Field of Classification Search
CPC ............ A61B 17/0493; A61B 2/08; A61B 2017/00358; A61B 2017/06052
See application file for complete search history.

(56) References Cited

U.S. PATENT DOCUMENTS

| | | | | |
|---|---|---|---|---|
| 5,741,299 | A | * | 4/1998 | Rudt ................ A61B 17/0493 606/224 |
| 5,897,591 | A | * | 4/1999 | Kobayashi ............... A61F 2/08 623/13.11 |
| 6,342,060 | B1 | * | 1/2002 | Adams ............... A61B 17/1146 606/151 |
| 2002/0077631 | A1 | * | 6/2002 | Lubbers ............... A61F 2/0811 606/232 |
| 2009/0048616 | A1 | * | 2/2009 | Gonzalez-Hernandez ................ A61B 17/1146 606/148 |
| 2009/0131980 | A1 | * | 5/2009 | Wiesman ........... A61B 17/1146 606/228 |
| 2011/0087248 | A1 | | 4/2011 | Steffen |
| 2011/0112532 | A1 | | 5/2011 | Steffen |
| 2011/0172706 | A1 | * | 7/2011 | Kappel ............ A61B 17/06128 606/223 |
| 2012/0071975 | A1 | * | 3/2012 | Gonzalez-Hernandez ................. A61B 17/1146 623/13.11 |
| 2012/0226296 | A1 | * | 9/2012 | Bindra ............... A61B 17/1146 606/151 |
| 2013/0041451 | A1 | * | 2/2013 | Patterson ................ A61F 2/97 623/1.12 |
| 2013/0144310 | A1 | | 6/2013 | Gordon et al. |
| 2014/0024885 | A1 | | 1/2014 | Sudekum |
| 2015/0282812 | A1 | | 10/2015 | Gonzalez-Hernandez |

FOREIGN PATENT DOCUMENTS

| | | |
|---|---|---|
| CN | 106976240 A | 7/2017 |
| EP | 11373671 B1 | 3/2005 |
| EP | 2108316 A1 | 10/2009 |
| WO | WO2000/33746 A1 | 6/2000 |
| WO | WO2003/003931 A1 | 1/2003 |
| WO | WO2018/109494 A1 | 6/2018 |

OTHER PUBLICATIONS

International Search Report and Written Opinion of the International Searching Authority, dated Dec. 17, 2019, for corresponding International Application No. PCT/GB2019/051686, 27 pages.
Bhatti et al., "Tendon retrieval in zone I and II Injury: a visit of new technique," *Injury Extra*. 2006; vol. 37, pp. 444-446.
Ersek et al., "The flexible tendon retriever," *Hand Surg Am* 1985; vol. 10(3); p. 415.
Fennell et al., "Principles of Tendon Repair," Orthopaedics III: Upper Limb, *Surgery*, vol. 34, Issue 3, Mar. 2016, pp. 152-156.
Hettiaratchy et al., "Flexor tendon retrieval: another trick," *Plast Reconstr Surg.*, 2002; vol. 109(6); pp. 2156-2157.
Hill, et al., "Endoscopic retrieval of severed flexor tendons: a study of technique using cadaveric hand," *Ann Plast Surg.*, 1997; vol. 38, pp. 446-448.
Iwuagwu et al., "A simple tendon retrieval method," *J Hand Surg* (Br) 2004; vol. 29, pp. 191-193.
Kamath et al., "A simple, semirigid, and surgeon-friendly tendon retriever and flexor sheath dilator," *Hand Surg Am* 2007; vol. 32(2); pp. 269-273.
Kilgore et al., "Atraumatic flexor tendon retrieval," *Am J. Surg.* 1971; vol. 122, pp. 430-431.
Kleinert et al., "Primary repair of zone two flexor tendon Lacerations," A.A.O.S. Symposium on Tendon Surgery in the Hand., 1975, pp. 91-104.
Oztnrk et al., "Atraumatic Flexor tendon retrieval-a simple method," *Annals of Surgical Innovation and Research*, 7:11, 2013, 4 pages.
DG Pennington, "Atraumatic retrieval of the proximal end of a severed digital flexor tendon," *Plast Reconstr Surg.*, 1977; 60, pp. 468-469.
Rudge and James, "Flexor Tendon Injuries in the Hand: A UK Survey of Repair Techniques and Suture Materials—Are We Following the Evidence?", ISRN Plastic *Surgery*, 2014.
Sourmelis, et al., "Retrieval of the retracted flexor tendon," *J Hand Surg Br.*, 1987; vol. 12; pp. 109-111.

* cited by examiner

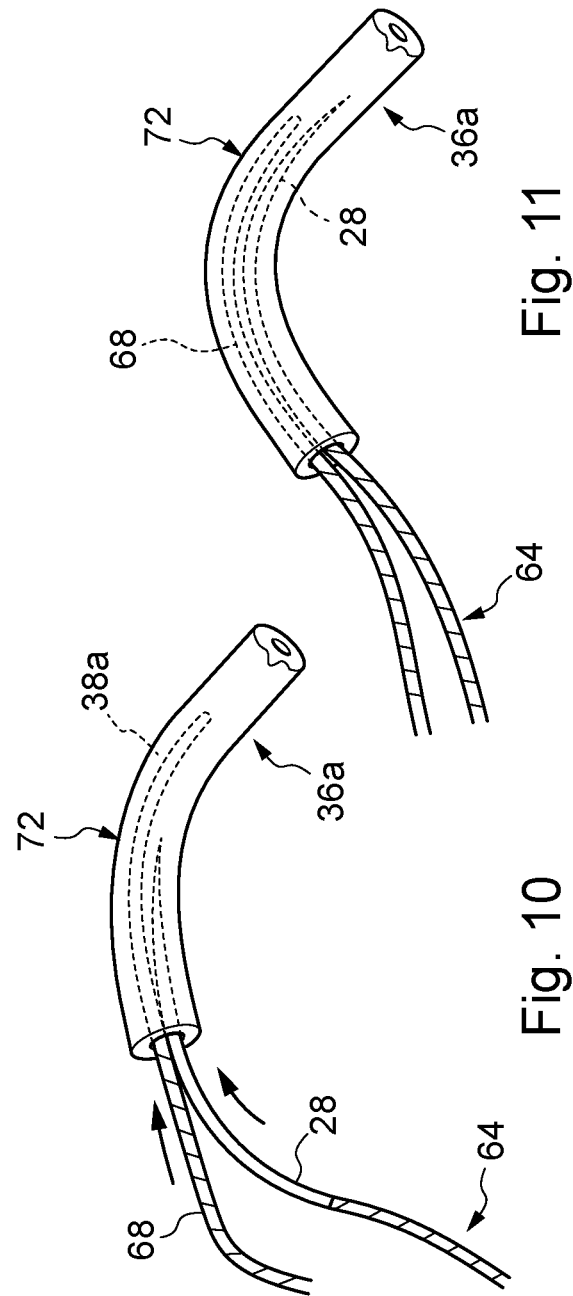

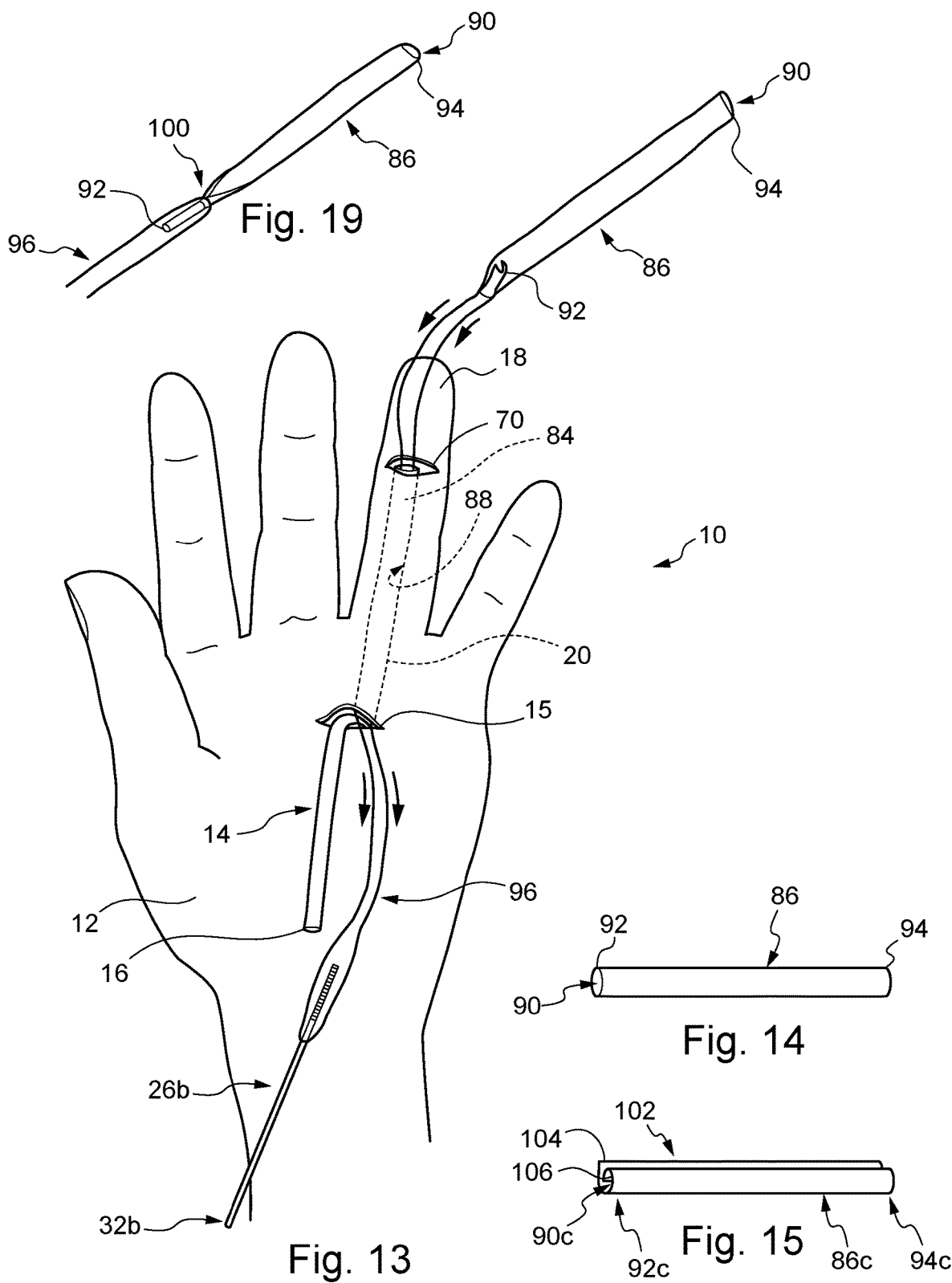

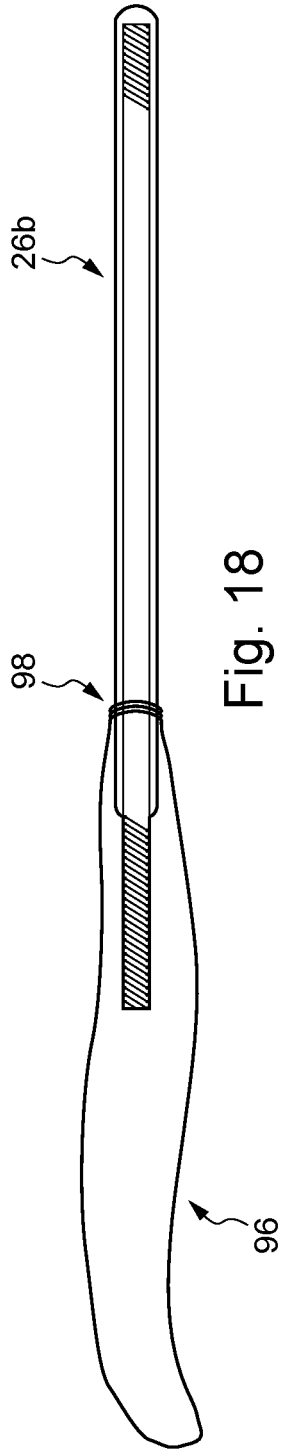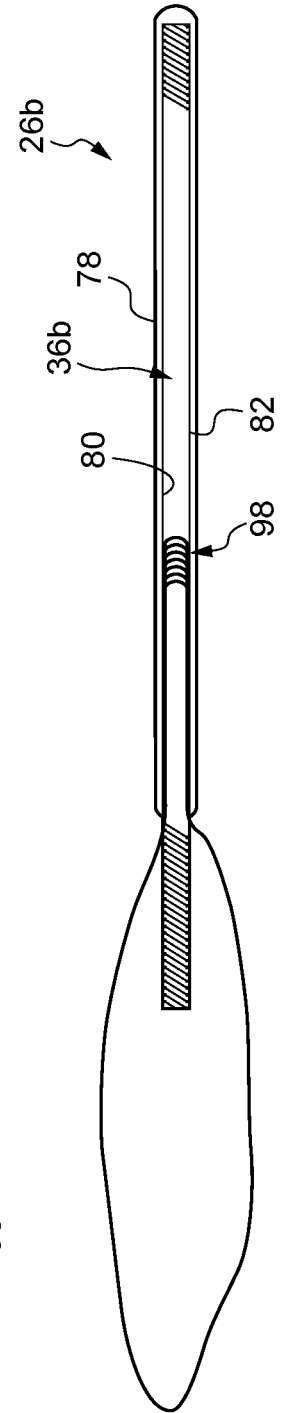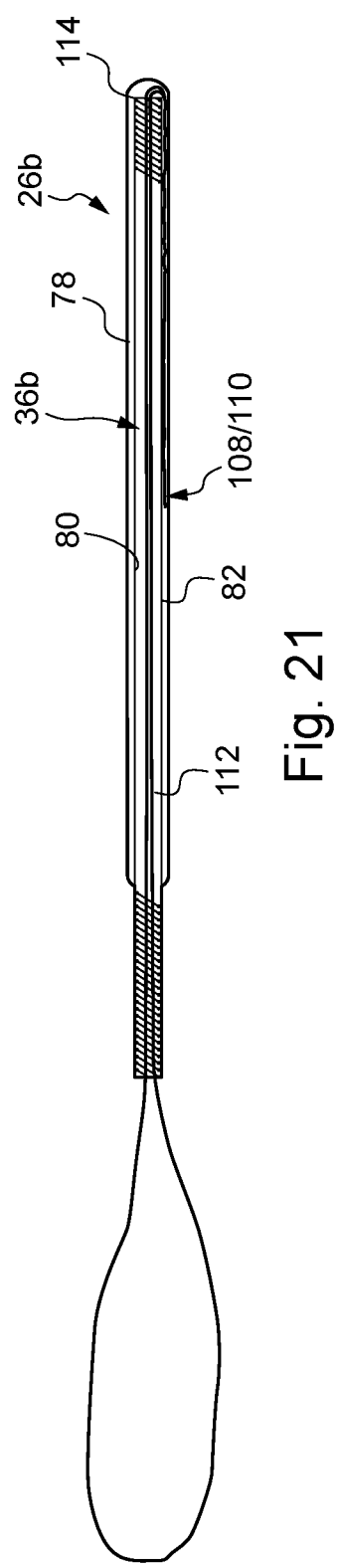

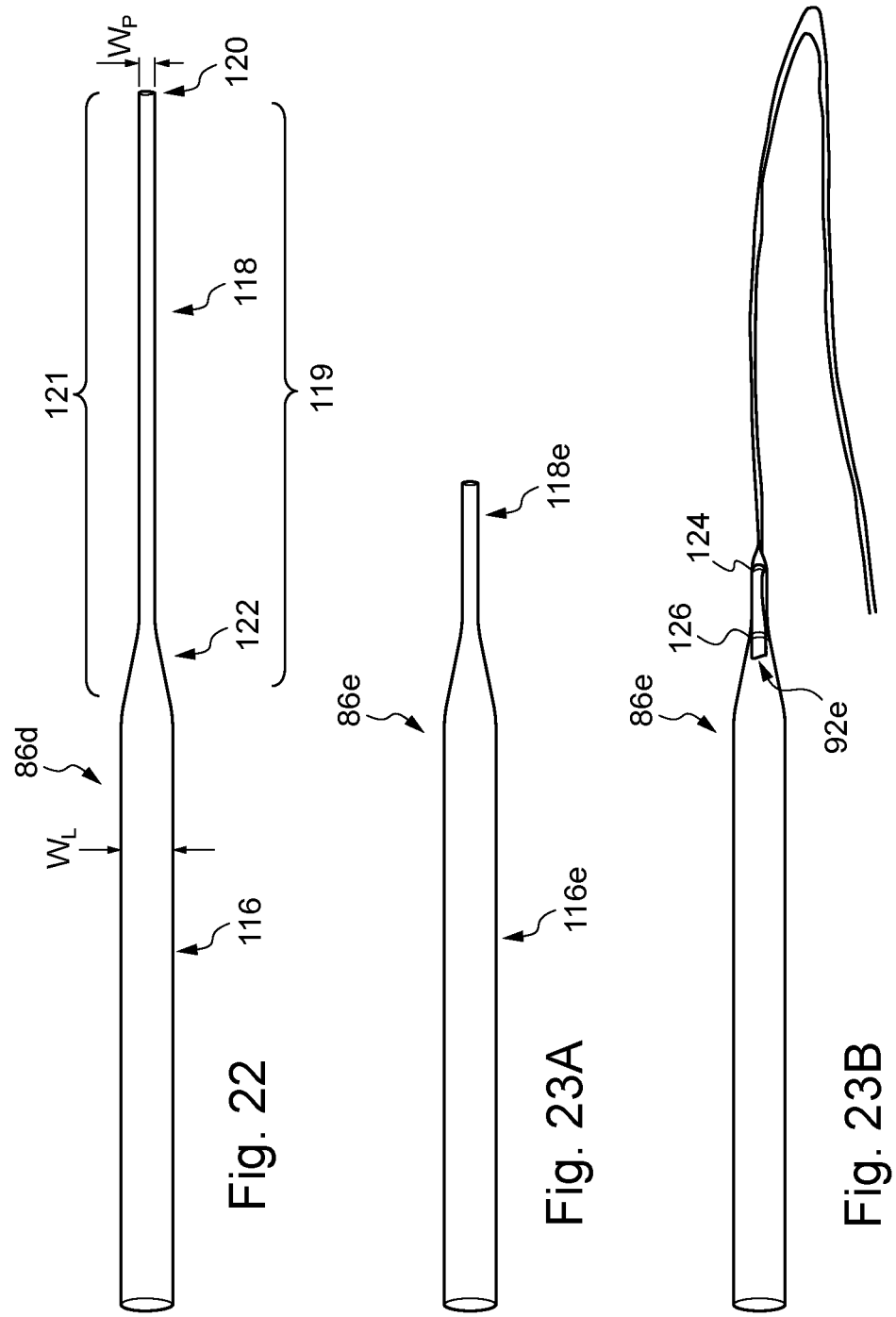

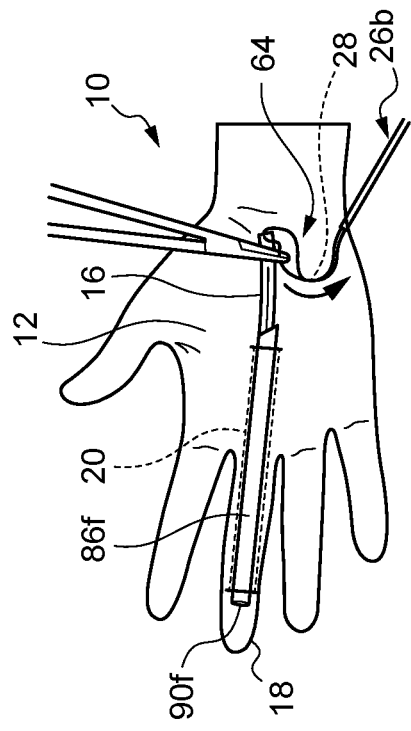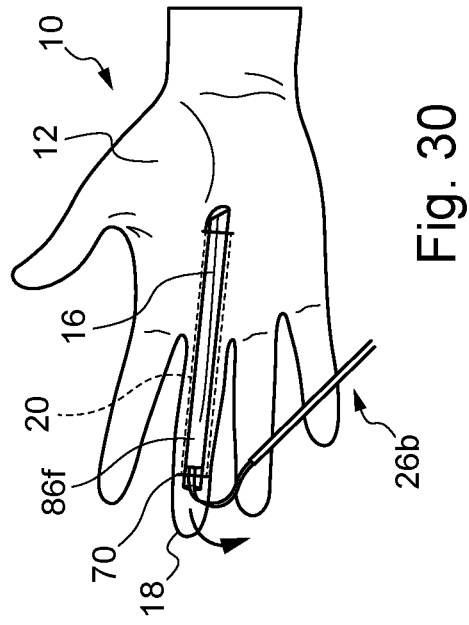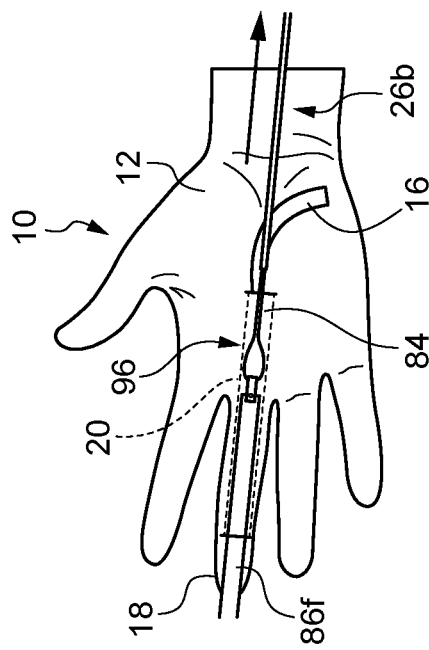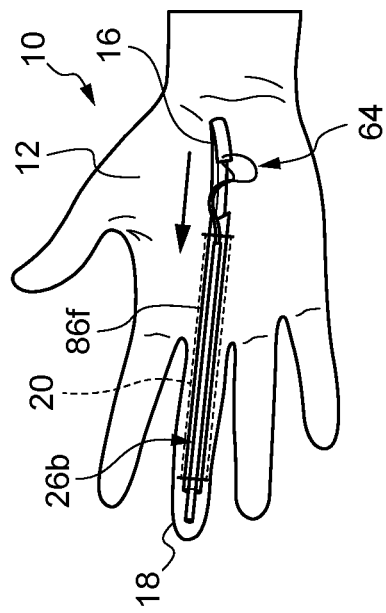

DEVICE, ASSEMBLY AND METHOD FOR USE IN TENDON REPAIR

CROSS-REFERENCE TO RELATED APPLICATIONS

The present application claims the benefit of and priority to United Kingdom Application Nos. GB1809949.9, filed Jun. 18, 2018, GB1820699.5, filed Dec. 19, 2018, and GB1901357.2, filed Jan. 31, 2019, all of which applications are incorporated herein by reference.

FIELD

The present invention relates to a needle covering and carrying device for covering a needle and carrying the needle within a tendon sheath. The present invention also relates to an assembly for use in repairing a severed tendon, the assembly comprising a needle and the needle covering and carrying device, and a method of repairing a severed tendon.

BACKGROUND

Injuries to the hand are common. Rudge and James (2014) in their study entitled "Flexor "Tendon Injuries in the Hand: A UK Survey of Repair Techniques and Suture Materials—Are We Following the Evidence?" (ISRN Plastic Surgery) stated that hand injuries account for around one-fifth of all presentations to the emergency department in most hospitals in the United Kingdom, and cost over £100 m per year to treat.

Flexor and extension tendons in the hand extend through tendon sheaths, within which the tendons are movable as the hand is flexed. Injuries to the hand of a human being often result in tendon damage, frequently involving severing of one or more of the tendons.

Tendon injuries are categorised within one of five different Zones of the hand. Zone 1 comprises the flexor digitorum profundus (FDP) tendon distal to insertion of the flexor digitorum superficialis (FDS) tendon. Zone 2 ("no man's land") comprises insertion of the FDS tendon to the proximal edge of the A1 pulley, which pulley is a cruciform structure beneath which the tendon sits. Zone 3 is in the palm, and comprises the proximal edge of the A1 pulley to the distal edge of the carpal tunnel.

When a finger injury occurs, resulting in a tendon being severed in Zone 1 or Zone 2, the tendon tends to retract towards the palm (Zone 3). A severed portion of the tendon remains in the tendon sheath within the finger, beyond the area where the tendon has been severed. Performing a repair on the severed tendon requires that the stump of the retracted tendon be drawn back along the tendon sheath, before being sutured to the stump of the tendon portion remaining within the finger.

Despite well-developed surgical techniques and suture materials being available, injuries to flexor tendons within Zone 2 of the hand still represent a significant challenge to hand surgeons. There is active interest in techniques to improve outcomes within the surgical community.

Ozturk et al., in the Annals of Surgical Innovation and Research 2013, 7:11, report and comment on various techniques that have been described in literature for the delivery of a retracted proximal tendon stump to a repair site, including the milking of the proximal tendon stump (Kleinert, 1975 [1]), suction (Pennington, 1977 [2]), use of rigid and flexible tendon retrievers (Ersek & Gadaria, 1985 [3]), skin hooks (Kamath & Bhardwa, 2007 [4]), steel wires (Iwuagwu & Gupta, 2004 [5]), aneurismal needle (Hettiaratchy & Titley, 2002 [6]), tendon suture side to side to a catheter (Sourmelis & McGrouther, 1987 [7]) and endoscopic tendon retrieval Hill, Wells & Prevel [8]).

Flexor tendon repair in zone 2 requires an atraumatic tendon retrieval technique with meticulous handling of the tendon stumps and minimal damage to the surrounding tendon sheath, because of the problematic nature of tendon healing without adhesions in this zone. There are various techniques described for flexor tendon retrieval beneath the tendon pulleys. Rigid and flexible tendon retrievers have been found to create additional crush injury to the severed tendon stump which causes additional fibrosis and altered tendon healing (Kamath & Bhardwa, 2007; Iwuagwu & Gupta, 2004).

Hettiaratchy and Titley described placing a core suture in the tendon stump and using an aneurysm needle to thread the suture through the pulleys, pulling the tendon out with the suture. This technique may not suitable to use for tendons retracted into the palm, and requires additional windowing of the sheath, which results in additional damage.

Other methods which involve passing a silastic tube through the tendon sheath and then suturing the proximal tendon stump to the tube side to side or end to end, or alternatively placing the tendon within its lumen, have been described (Sourmelis & McGrouther 1987; Hill, Wells & Prevel 1997; Kilgore, Adams & Newmeyer, 1971 [9]). However, all of these methods potentially create a bulky mass, which may harm the tendon sheath during passage along it. Also, all of these methods require that the tendon stumps be sutured multiple times, which may fray the tendon tip and make the repair more difficult.

For good results to be achieved it is vital that the surgical repair is performed with atraumatic handling of the severed tendon stumps and minimal damage to the tendon sheath, in order to prevent postoperative adhesions and ruptures in this area. Accordingly, it is extremely desirable to be able to draw the tendon through its sheath with a 'needled' suture that can be continued as part of the definitive repair.

Bhatti & Adeniran (2006) [10] described a technique of suturing the proximal tendon stump at the distal palmar crease with a straight needle and polypropylene suture, and using a 14-gauge plastic cannula with stylet, acting like a conduit for the passage of the straight needle to the finger. Traction of the suture end results in delivery of the cut tendon stump. However, the straight needle is not always available in the operating room. More important to note is that it is difficult to complete a modified Kessler stitch using a straight needle, or many of the other popular tendon suture techniques, which use curved needles.

Ozturk et al. (2013) present a simple and relatively atraumatic technique that facilitates passing of the retracted flexor tendon through the pulleys in zone 2. The authors sutured the proximal tendon stump at the distal palmar crease with a 3-0 polypropylene suture, and used a 14-gauge plastic feeding tube, acting like a conduit for the passage of a straightened needle to the finger.

US Patent Publication No. US-2013/0144310A1 discloses an apparatus for reattaching severed tendon stumps in the hand. The disclosed apparatus (see FIG. 1) is complex and comprises numerous components including a pulley catheter which is connected to a flanged catheter by a connector. The pulley catheter is of a polymeric material with sufficient rigidity (so that it can be pushed through tendon pulleys), and the flanged catheter is of a softer polymeric material such as a silicone. Further, the apparatus also comprises a tendon anchor including a short straight needle which is attached to an end of a multifilament cable, the cable being unwound into separate sutures from a sleeve located at an intermediate point of the cable. Curved needles (see labels 114a-g) are attached to the end of each suture. In use, the pulley catheter is fed into an incision in the palm and along a tendon sheath beneath tendon pulleys (see FIG. 2 A). The flanged catheter is then connected to the pulley catheter and drawn part-way into the tendon sheath (see FIG. 2B). A tendon stump in the palm is then delivered to the surface and the straight needle of the tendon anchor placed into and pulled through the stump. The curved needles are then used to stich the tendon repair device to the stump, a pair of sutures being tied in a knot and stitched to the tendon using criss-cross locking stiches formed using further curved needles and sutures. Excess suture material and the curved needles are then removed (see FIGS. 2D&E). The straight needle is then inserted into the flange of the flanged catheter and advanced until the tendon stump is in the flanged portion. The surgeon then grasps the straight needle and pulls the needle, attached cable, flanged catheter and tendon stump through the pulley system and out of a wound in the finger. A further tendon anchor of a similar structure is then attached to the tendon stump in the finger in the same way as described above, and the needles of the two anchors inserted through bores of a connector, passing in opposite directions. Traction is then applied to the tendon stumps to pull them together with the connector buried in the tendon ends. A crimping tool is then used to crimp the connector and extra lengths of the cables are cut. An apparatus like the pulley catheter is also disclosed, and is described as a dilation catheter which has a wall thickness sufficient to make the entire catheter sufficiently stiff to be pushed through the pulley system, and to serve the purpose of dilating the pulleys against their natural size.

The apparatus disclosed in US-2013/0144310A1 is complex and the procedure for tendon repair described is cumbersome. The system suffers from numerous disadvantages. These include that the tendon anchor is complex to assemble, and its use in a surgical procedure is complicated and time-consuming. Manipulating the straight needle and trailing cable to insert it through the tendon stumps is challenging, and requires the use of various clamps to hold the tendon stumps in place. Advancing the tendon anchor along the flanged catheter is also challenging, since it is necessary to use the cable connected to the needle to advance it through the catheter. Furthermore, it is difficult to make the cable sufficiently rigid to achieve this without hampering the procedure for connecting the tendon anchor to the stumps. As the flanged catheter is of a relatively soft polymeric material, this presents a serious risk of the catheter being punctured by the needle when it is advanced along the catheter, which could result in the needle becoming jammed within the catheter, and potentially being misdirected into surrounding tissue. The pulley catheters are typically 120 mm long, of relatively small outer diameter (typically 2 mm), with a wall thickness of 0.5 mm thus having an internal diameter of 1 mm (see para. 0070). It would be difficult to push the straight needle through a pulley catheter of the above dimensions with a cable. The sleeves of the tendon anchors, and the connector that is used to connect the cables of the two anchors, are all buried within the tendon stumps. These components are therefore permanently located within the tendon stumps, which could hamper tissue ingrowth and effective repair of the tendon. In using the dilation catheter (see FIG. 13 A-C, and FIG. 14 A-E), it is possible that the user would over-dilate the pulleys, leading to potential damage and rupture of the pulleys. Apart from the danger of the risk of over dilating the pulleys and possible consequent damage to the same, the dilating section left within the tendon sheath must be of sufficient thickness to impart to it the necessary rigidity to achieve the intended dilation of the pulleys. Were the above dilating section collapsible it would not be possible to use it to dilate the pulleys. This particular feature is of relevance to the present disclosure as will be shown later.

From the above it is evident that there is a need to improve upon the existing devices and surgical techniques employed in tendon repair.

SUMMARY

According to a first aspect of the present disclosure, there is provided a needle covering and carrying device for covering a curved needle and carrying the needle within a lumen of a tendon sheath, the device comprising an elongate element having:
  a first end;
  a second end opposite the first end; and
  a body extending between the first and second ends, the body defining an internal cavity for accommodating a curved needle so that at least a penetrating tip of the needle is disposed within the body, to protect the tendon sheath from damage through contact with the tip during passage of the needle within the sheath;
  in which the body is:
  A. substantially rigid, having a curved shape so that it can accommodate the curved needle; or
  B. deformable, and capable of being deformed into a curved shape so that it can accommodate the curved needle.

Surgical techniques for the repair of damaged tendons, particularly in the hand, would greatly benefit from the use of a curved needle. For example, use of a curved needle improves the ability of a surgeon to suture stumps of a severed tendon together.

The present application discloses embodiments that facilitate the passage of a curved needed within a tendon sheath whilst restricting, or even avoiding, damage to the sheath through contact with the needle. The needle can be drawn through the tendon sheath trailing a tendon stump, so that the stump can be sutured to the stump of a second portion of the tendon. In tendon repair surgery on the hand, the second portion of tendon may reside in the finger.

Reference is made herein to a needle covering and carrying device for covering a curved needle and carrying the needle within a tendon sheath. It will be understood that the tendon sheath may be one of many different sheaths, ducts or conduits found in the human (or animal) body. However, disclosed embodiments have a particular use in relation to surgery on the hand, in which the tendon sheath will be the sheath of a tendon found in the hand (e.g. the FDP or FDS tendon).

The device, in particular the cavity, may be adapted to receive the entire needle. The device may form an envelope or shroud for the needle.

The cavity may extend from the first end of the device to the second end of the device.

The first end of the body may be a leading end and the second end may be a trailing end. At least one of the first and second ends may be open, or at least partially open, and may communicate with the cavity. This may facilitate insertion of the needle into the cavity through the open end, and/or may allow a suture connected to the needle to exit the body.

The body may serve for transporting the needle along or within the sheath. The first end may be adapted to be inserted into the tendon sheath and directed along it. The body may form a threading element (hereinafter called a threader) adapted to transit along the sheath. In use, the body may comprise a portion defining the threader and a portion which forms a cover for the needle. The threader portion may be substantially straight, which may facilitate transit within the sheath. In option A, the cover portion may have the curved shape. In option B, the cover portion may be capable of being deformed into the curved shape.

The cavity may extend part way along a length of the body. The cavity may extend from one of the first and second ends in a direction towards the other one of the first and second ends. Where the second end is a trailing end, the cavity may extend from the second end towards the first end.

The cavity may be disposed between the first and second ends.

The body may comprise a coupling for connecting the device to a transportation assembly used to transport the device within the sheath. The transportation assembly may comprise an elongate threading element (threader) and a flexible connecting component connected to the threader, the connecting component being adapted to be connected to the coupling of the body. The connecting component may be flexible, may be a cord, wire, filament or the like, and may be a suture. The coupling may be an eye, hoop or the like mounted on or connected to the body.

The body may be generally tubular. The body may be generally cylindrical, and may have a circular shape in cross-section.

The device may comprise an outer sheath, sleeve or covering. The outer sheath may ease passage of the device within the tendon sheath. The outer sheath may be of a plastics (suitably polymeric) or elastomeric material, which materials may have a low coefficient of friction, to facilitate passage of the device within the tendon sheath. The outer sheath may have an inner surface which is disposed in contact with an outer surface of the body. The outer sheath may be tubular. The outer sheath may extend at least part way along a length of the body. The outer sheath may extend in a direction from one of the first and second ends of the device in a direction towards the other one of the first and second ends. Where the first end is a leading end, the outer sheath may extend from the first end along the body in a direction towards the second end. The outer sheath may cover the first end. Where the second end is a trailing end, the second end may be exposed, and so may not be covered by the outer sheath. A portion of the body may define the cavity. The portion may be exposed, and so may not be covered by the outer sheath. The outer sheath may therefore extend from the first end along the body to said portion.

A needle covering and carrying device according to option A may have one or more of the following features.

The cavity may be curved. The cavity may have a curved shape which substantially matches that of the curved needle. The needle may have a radius of curvature, and the cavity may have a radius of curvature. The radius of curvature of the cavity may substantially match that of the needle.

The body may comprise a first body part, and a second body part which is connected to the first body part. The first and second body parts, when connected, may form the body. At least one of the first and second body parts may be movable relative to the other one of the first and second body parts, and may be movable between an open position in which the needle can be inserted into the cavity, and a closed position in which the cavity is closed. The body may be lockable in the closed position. The device may comprise a clip, clamp or lock for locking the body in the closed position. At least one of the first and second body parts may be pivotable relative to the other one of the first and second body parts, such as via a hinge. The hinge may be a living hinge.

Suitable materials for the body may be selected from the group comprising: plastics, suitably polymeric materials; metals; and metal alloys.

A needle covering and carrying device according to option B may have one or more of the following features.

At least part of the body of the device, or optionally only a part of the body of the device, may be plastically deformable. A part of the body defining the cavity may be plastically deformable. The entire body may be plastically deformable. The device may be capable of being bent into a required shape (to accommodate the curved needle), which may occur either on insertion of the needle into the cavity, or in advance such as by appropriate manipulation of the body to have a shape which suits a particular needle.

At least part of the body of the device, or optionally only a part of the body of the device, may be elastically deformable. A part of the body defining the cavity may be elastically deformable. The entire body may be elastically deformable. The device may be capable of adopting a curved shape when the needle is inserted into the cavity. The body may be elastically deformable from an undeformed or starting configuration, which may be a substantially straight and/or unstressed configuration, to a deformed or deployed configuration, which may be a curved configuration. The body may return to the undeformed configuration when the needle is removed from the cavity. The body may be of a metal or metal alloy material.

The body, and optionally the device, may take the form of a spring. The spring may be a tension spring or sprung member. The spring may be helically wound. The spring may comprise a plurality of turns or coils, which may be arranged so that the turns or coils are in abutment (which may be close abutment), at least in a rest state. The spring may be of a metal or metal alloy material, such as a stainless steel material, although plastics (suitably polymeric) materials may be suitable. The body, particularly where it takes the form of a spring, may be deformable in multiple directions, relative to a main axis of the body (in an undeformed state). The body may therefore be deflectable in any desired direction away from the main axis (for example a radial direction). The body may therefore demonstrate a high degree of compliance.

The body may comprise a sidewall. An opening may be formed in the sidewall which communicates with the cavity. The needle may be insertable into the cavity through the opening.

Further features of the needle covering and carrying device of the first aspect of the present disclosure may be derived from the text set out elsewhere in this document, particularly in or with reference to the surgical assemblies of the second and third aspects of the present disclosure.

According to a second aspect of the present disclosure, there is provided an assembly for use in repairing a severed tendon, the assembly comprising:

a curved needle; and
a needle covering and carrying device for covering the curved needle and carrying the needle within a lumen of a tendon sheath, the needle covering and carrying device comprising an elongate element having:
a first end;
a second end opposite the first end; and a body extending between the first and second ends, the body defining an internal cavity for accommodating a curved needle so that at least a penetrating tip of the needle is disposed within the body, to protect the tendon sheath from damage through contact with the tip during passage of the needle within the sheath;
in which the body is:
A. substantially rigid, having a curved shape so that it can accommodate the curved needle; or
B. deformable, and capable of being deformed into a curved shape so that it can accommodate the curved needle.

Further features of the assembly of the second aspect of the present disclosure, particularly of the needle covering and carrying device, may be derived from the text set out elsewhere in this document, particularly in or with reference to the needle covering and carrying device of the first aspect of the present disclosure.

According to a third aspect of the present disclosure, there is provided an assembly for use in repairing a severed tendon, the assembly comprising:
a threading element adapted to transit along a lumen of a tendon sheath; and
a liner for lining an internal surface of the tendon sheath, the liner defining an internal passage along which a tendon stump can pass during transit along the lumen, the liner acting to restrict contact between the tendon stump and the internal surface of the tendon sheath;
in which the liner is adapted to be releasably coupled to the threading element so that it can be drawn into the tendon sheath by the threading element and located within the lumen, and then released from the threading element so as to reside within the lumen.

Reference is made to a threading element, which is an element that is adapted, by appropriate shaping (e.g. elongate and of relatively small diameter or width) and/or selection of materials (e.g. plastically deformable/malleable or elastically deformable), to pass along the narrow lumen of the tendon sheath, and so to transit the sheath trailing the liner.

The threading element may serve for drawing the liner into the lumen of the tendon sheath, and may then be released from the liner so that the liner can be disposed within the lumen, in which position the liner may serve to restrict (and optionally to entirely prevent) contact between the tendon stump and the internal surface of the tendon sheath. This may restrict (and potentially avoid) damage to the tendon stump during transit along the lumen, which could otherwise fray, making it difficult to subsequently connect it to a further stump of the tendon in a tendon repair procedure of the type described above.

Whilst the liner has a particular use in restricting contact between a tendon stump and the internal surface of the tendon sheath (and optionally preventing contact), the liner may also serve for restricting (and potentially avoiding) contact between other objects and the internal surface of the tendon sheath, including but not restricted to the threading element itself, for example during return transit along the lumen.

The assembly may comprise a needle covering and carrying device for covering a curved needle and carrying the needle within the lumen of a tendon sheath. The needle covering and carrying device may comprise an elongate element having:
a first end;
a second end opposite the first end; and
a body extending between the first and second ends, the body defining an internal cavity for accommodating a curved needle so that at least a penetrating tip of the needle is disposed within the body, to protect the tendon sheath from damage through contact with the tip during passage of the needle within the sheath.

The body may be deformable, and capable of being deformed into a curved shape so that it can accommodate the curved needle. The body may be substantially rigid, having a curved shape so that it can accommodate the curved needle.

The body may form the threading element. In use, the body may comprise a portion defining the threading element and a portion which forms a cover for the needle.

The liner may be elongate. The liner may take the form of a sheath. The liner may be substantially tubular, and may have any suitable cross-sectional shape. The liner may be collapsible and/or adapted to be flattened for easy insertion into and transit along the lumen of the tendon sheath. This may be achieved by selection of suitable materials for the liner, and the provision of a liner having a wall thickness which is suitable for collapsing/flattening. The liner may comprise an outer surface adapted to contact the internal surface of the tendon sheath, and an inner surface which defines the internal passage, and which may be contacted by the tendon stump during transit along the lumen.

The liner may comprise a slit, and may be slit along an entire length of the liner from a first axial end to a second axial end. The provision of a liner having such a slit may facilitate removal of the liner from the lumen following completion of a tendon repair procedure in which tendon stumps are connected to restore function to a severed tendon, the slit enabling the liner to be drawn over the repaired tendon leaving the tendon in place within the lumen of the tendon sheath. The liner may be adapted to be rolled or coiled, for example about a longitudinal axis, so as to define the internal passage. Rolling or coiling of the liner may form it into the shape of a tube. Where the liner is slit, the liner may comprise a first lateral edge and a second lateral edge. Where the liner is rolled or coiled, a portion of the liner comprising one of the lateral edges may overlap a portion of the liner comprising the other lateral edge. The liner may be of a plastics (suitably polymeric) or elastomeric material, which materials may have a low coefficient of friction, to facilitate insertion into the lumen of the tendon sheath, and transit of the tendon stump along the internal passage of the liner.

The liner may comprise a sheath lining portion adapted to be located within the lumen of the tendon sheath, and a pulling portion extending from the lumen lining portion and adapted to be used to pull the sheath lining portion into and along the lumen. The pulling portion may have a length which greater than, or substantially equal to, a length of the sheath lining portion. The threading element may be adapted to be coupled to the pulling portion, and may be used to draw the pulling portion into the lumen. The pulling portion may subsequently be used to draw the sheath lining portion into the lumen, by pulling an end of the pulling portion out of the lumen. The pulling portion may be adapted to be gripped by a user to pull the sheath lining portion into the lumen. The sheath lining portion may be substantially tubular (including where it comprises a slit and is coiled as discussed above). The pulling portion may comprise one or more elongate strips, legs or the like, which may extend from the substantially tubular lumen lining portion. Alternatively the pulling portion may also be tubular, and may be of a smaller diameter or width than the lumen-lining portion. The pulling portion may be integral with the lumen-lining portion.

The assembly may comprise at least one further liner, for lining an internal surface of a further tendon sheath. The further liner may also be adapted to be releasably coupled to the threading element so that it can be drawn into the further tendon sheath by the threading element and located within the lumen of the further tendon sheath, and then released from the threading element so as to reside within the lumen. The further liner may have a use in a tendon repair procedure of a further tendon, for example in the same or in a second (and optionally further) finger.

The threading element may take the form of a spring. The spring may be a tension spring or sprung member. The spring may be helically wound. The spring may comprise a plurality of turns or coils, which may be arranged so that the turns or coils are in abutment (which may be close abutment), at least in a rest state. The spring may be of a metal or metal alloy material, such as a stainless steel material, although plastics (suitably polymeric) materials may be suitable.

The threading element may comprise an outer sheath, sleeve or covering. The outer sheath may ease passage of the threading element within the tendon sheath. The outer sheath may be of a plastics (suitably polymeric) or elastomeric material, which materials may have a low coefficient of friction, to facilitate passage of the device within the tendon sheath. The outer sheath may have an inner surface which is disposed in contact with an outer surface of the body.

As discussed above, the body may comprise a portion defining the threading element and a portion which forms a cover for the needle. The cover may have the same structure as that of the threading element and may be continuous with it. Where the threading element is formed of a spring as mentioned above (optionally comprising a plurality of coils), the outer (covering) sheath may give the threading element a measure of rigidity so it can be pushed through the lumen of the tendon sheath. A stiffness or flexural modulus of the part of the threading element covered by the outer sheath may be greater than a part which is not covered by the outer sheath. Thus the part of the threading element which is covered by the outer sheath may be stiffer than the part that is not covered.

The assembly may comprise a flexible connecting component for releasably connecting the threading element to the liner. The flexible connecting component may be a cord, wire, filament or the like, and may be a suture. Where the assembly comprises a needle covering and carrying device (in which the body of the device forms the threading element), the flexible connecting component may be a suture connected to the needle.

Suitably, the needle will be removed from the covering and carrying device before the suture is used to draw the liner into the lumen of the tendon sheath.

The flexible connecting component may be releasably connected to the threading element by tying, such as by whipping the connecting component to/around the threading element. Where the threading element comprises an outer sheath, the flexible connecting component may be releasably connected to the threading element by trapping a part of the connecting component between an outer surface of the body and an inner surface of the outer sheath. Where the threading element takes the form of a spring, the spring may define an internal passage and may have an open end, and the flexible connecting component may pass up the internal passage of the spring to the open end of the spring, before exiting from the open end and passing away from the open end between an outer surface of the spring and an inner surface of the outer sheath.

The flexible connecting component may be formed into a loop. The liner, in particular the pulling portion (for example at least one of the one or more elongate strips) may be folded over the loop, and the flexible connecting component may be secured relative to the liner by tying, such as by whipping the connecting component to/around the liner.

The liner may be coupled to the threading element so as to define two tendon sheath lining portions. The liner may have a first end and a second end, and coupling may be achieved by connecting the liner to the threading element at a point along a length of the liner between the first and second ends, suitably at or proximate a midpoint of the liner. Coupling may be achieved by folding the liner at said point, about/to the threading element or the connecting component. A length of each tendon sheath lining portion may be substantially the same, although the lengths could be different, provided that they are sufficiently long to line the tendon sheath (or at least the part of the tendon sheath extending between surgical openings). The tendon sheath lining portions may serve for receiving the tendon stumps of respective tendons. It is well known that tendon sheaths in the finger can accommodate more than one tendon. The assembly may therefore enable two tendon sheath lining portions to be located in a single tendon sheath, for use where both of the finger tendons are to be repaired.

The liner may comprise a first end, a second end, and a body extending between the first and second ends. The liner may comprise a first tendon sheath lining portion extending from the first end towards a part of the liner disposed between the first and second ends, and a second tendon sheath lining portion extending from the second end towards the part disposed between the first and second ends. The first and second tendon sheath lining portions may each have a width, and said part may have a width which is less than the width of the first and second tendon sheath lining portions. A width of the first tendon sheath lining portion may be the same as (or substantially the same as) a width of the second tendon sheath lining portion. Said part may comprise a main section of substantially constant width; a first transition section extending between the main section and the first tendon sheath lining portion; and a second transition section extending between the main section and the second tendon sheath lining portion. The transition sections may have a width which progressively increases from the width of the main section to the width of the respective tendon sheath lining portion. Said part may comprise a first transition section extending from the first tendon sheath lining portion; and a second transition section extending from the second tendon sheath lining portion and coupled to the first transition section. The transition sections may have a width which progressively increases from a width defined at or by an intersection between the transition sections, to the width of the respective tendon sheath lining portions.

The liner may be adapted to be releasably coupled to the threading element (in particular the flexible connecting component) in or at said part. Where the flexible connecting component is formed into a loop, the liner may be releasably couplable to the threading element by folding it over the loop at or about said part. The first and second tendon sheath lining sections may be adapted to be separated from one another, suitably by severing the liner so as to remove said part.

Further features of the assembly of the third aspect of the present disclosure, particularly of the threading element and the needle covering and carrying device, may be derived from the text set out elsewhere in this document, particularly in or with reference to the needle covering and carrying device of the first aspect of the present disclosure and the assembly of the second aspect of the present disclosure, or the methods and assemblies defined in the fourth to seventh aspects.

According to a fourth aspect of the present disclosure, there is provided a method of retrieving a tendon stump of a severed tendon, which may be part of a method of repairing a severed tendon, the method comprising the steps of:
- passing a curved needle connected to a suture through a first tendon stump, to connect the suture to the first tendon stump;
- providing a needle covering and carrying device comprising an elongate element having a first end, a second end opposite the first end, and a body extending between the first and second ends, the body defining an internal cavity;
- locating at least a penetrating tip of the curved needle within the cavity defined by the body, so that the tip is covered by the device;
- inserting the first end of the elongate element into the tendon sheath;
- directing the elongate element along the tendon sheath carrying the needle and the suture, towards a second tendon stump spaced along the sheath from the first tendon stump;
- removing the needle covering and carrying device from the tendon sheath;
- removing the needle from the cavity in the body;
- drawing the first tendon stump along the tendon sheath using the suture, to a position proximate the second tendon stump, so that the tendon stumps can be connected.

The method may comprise locating a free end of the suture within the cavity defined by the body. Following removal of the elongate element from the tendon sheath, the method may comprise removing the needle and the end of the suture from the cavity in the body, optionally before drawing the first tendon stump along the tendon sheath.

The method may comprise passing the curved needle connected to the suture through the second tendon stump, to connect the suture to the second tendon stump; and manipulating the suture to connect the first tendon stump to the second tendon stump, and thereby repair the severed tendon.

The method may comprise locating the entire needle within the cavity (and so including a trailing end of the needle, which may be coupled to the suture), so that the entire needle is covered by the device.

The method may comprise removing the first tendon stump from the tendon sheath to expose the stump, and then connecting the suture to the first stump. The method may comprise removing the second tendon stump from the tendon sheath to expose the stump, and then connecting the suture to the second stump.

The method may comprise inserting the entire needle into the cavity in the body of the threader. The suture may pass out of the body through an opening, which may be provided in or by the second end.

The step of removing the device from the tendon sheath may comprise drawing the second end of the device out of the sheath.

Reference is made in this document to a tendon sheath of a tendon. It will be understood that the tendon sheath may comprise a number of sheath parts or portions which together form the sheath. This may particularly be the case in a surgical procedure, in which apertures may be formed in the tendon sheath so that the damaged tendon can be accessed.

The first tendon stump may be a proximal stump, and the second tendon stump may be a distal stump. In the context of a hand of a human, the distal end may be disposed closer to a tip of a finger containing the tendon. The assembly and method may have a use in surgery on other parts of the human or animal body, such as the foot.

Reference is made in this document to drawing of the first tendon stump to a position proximate the second tendon stump. It will be understood that this should typically be taken to mean that the first tendon stump is moved to a position in which it is sufficiently close to the second tendon stump that the stumps can be sutured together. This will usually involve removing the first tendon stump from the tendon sheath near the second tendon stump.

The method may comprise the step of lining an internal surface of the tendon sheath with a liner, the liner defining an internal passage along which the first tendon stump can pass during transit along the tendon sheath. The tendon sheath may be lined prior to carrying out the step of locating at least the penetrating tip of the curved needle within the cavity defined by the body, and may be carried out prior to carrying out the step of passing the curved needle trailing the suture through the first tendon stump.

The liner may be drawn into the tendon sheath by a threading element which can transit along a lumen of the tendon sheath. The threading element may be formed by the body of the covering and carrying device. The method may comprise releasably coupling the liner to the threading element. The liner may be released from the threading element following location within the lumen.

The step of inserting the first end of the elongate element into the tendon sheath may comprise inserting the first end into the internal passage of the liner. The step of directing the elongate element along the tendon sheath carrying the needle and the suture may comprise directing the elongate element along the internal passage of the liner. The step of removing the needle covering and carrying device from the tendon sheath may comprise removing the elongate element from the internal passage of the liner.

The method may comprise the step of removing the liner from the tendon sheath following passing of the curved needle connected to the suture through the second tendon stump. The liner may only be removed following manipulation of the suture to connect the first tendon stump to the second tendon stump, and thereby repair the severed tendon. The liner may comprise a slit, which may extend along an entire length of the liner from a first axial end to a second axial end, the slit facilitating removal of the liner from the lumen. The liner may be removed by sliding it laterally relative to the tendon, so that the tendon passes through or out of the slit.

The method may comprise the step of lining an internal surface of the tendon sheath with a liner which is coupled to the threading element so as to define two tendon sheath lining portions. The liner may have a first end and a second end, and may be coupled to the threading element at a point along a length of the liner between the first and second ends, suitably at or proximate a midpoint of the liner. The tendon sheath lining portions may serve for receiving the tendon stumps of respective tendons. The method may therefore be for repairing two severed tendons, which tendons are normally located within a single tendon sheath.

Further features of the method of the fourth aspect of the present disclosure, particularly relating to the needle covering and carrying device, may be derived from the text set out elsewhere in this document, particularly in or with reference to the needle covering and carrying device and assemblies of the first to third aspects of the present disclosure, or the methods and assemblies defined in the fifth to seventh aspects.

According to a fifth aspect of the present disclosure, there is provided a method of lining a tendon sheath of a severed tendon in preparation for performing a tendon repair procedure, the method comprising the steps of:

releasably coupling a threading element to a liner defining an internal passage;
  inserting the threading element into a lumen of a tendon sheath trailing the liner behind it;
  directing the threading element along the lumen of the tendon sheath, to draw the liner into the lumen;
  locating the liner in the tendon sheath so that it lines an internal surface of the tendon sheath;
  removing the threading element from the lumen of the tendon sheath; and
  releasing the liner from the threading element leaving the liner in place within the lumen of the tendon sheath, the liner serving to restrict contact between a tendon stump of a severed tendon and the internal surface of the tendon sheath during a subsequent tendon repair procedure.

Further features of the method of the fifth aspect of the present disclosure may be derived from the text set out elsewhere in this document, particularly in or with reference to the needle covering and carrying device and assemblies of the first to third aspects of the present disclosure, and the method of the fourth aspect of the present disclosure, or the assembly and method defined in the sixth and seventh aspects.

According to a sixth aspect of the present disclosure, there is provided an assembly for use in repairing a severed tendon, the assembly comprising:

an elongate threading element adapted to transit along a lumen of a tendon sheath, for covering a curved needle and carrying the needle within the lumen of the tendon sheath, the elongate threading element having:
    a first end;
    a second end opposite the first end; and
    a body extending between the first and second ends, the body defining an internal cavity for accommodating the curved needle to protect the tendon sheath from damage through contact with the needle during passage of the needle within the tendon sheath, the body being deformable into a curved shape so that it can accommodate the curved needle, the body optionally comprising a spring having a plurality of coils;
  a liner for lining an internal surface of the tendon sheath, the liner defining an internal passage along which a tendon stump coupled to the curved needle can pass during transit along the lumen, the liner preventing contact between the tendon stump and the internal surface of the tendon sheath, the liner optionally having:
    a collapsed, rest configuration in which the liner is adapted to be inserted into the lumen of the tendon sheath; and
    an expanded, operating configuration, the liner being movable to the expanded configuration by contact with the tendon stump;
  in which the liner is adapted to be releasably coupled to the elongate threading element so that it can be drawn into the tendon sheath by the threading element and located within the lumen, and then released from the threading element so as to reside within the lumen;
  and in which the elongate threading element, once released from the liner, is adapted to receive the curved needle, for covering and carrying the curved needle through the liner and along the lumen of the tendon sheath trailing the connected tendon stump.

The body may be defined by the spring. The body may have an outer surface, and the elongate threading element may comprise an outer sleeve having an inner surface which is disposed in contact (optionally close contact) with the outer surface of the body. The outer sleeve may extend part way along a length of the body from the first end. The outer sleeve may provide a degree of rigidity to the body (without overly restricting its ability to deform to transit along the lumen of the tendon sheath), which may facilitate insertion of the body into the tendon sheath, and pushing of the body along the lumen.

A portion of the body comprising the second end may be adapted to accommodate the curved needle, and the outer sleeve may extend from the first end to said portion of the body so that said portion is not covered by the outer sleeve. Leaving said portion of the body uncovered by the outer sleeve may provide the portion with greater flexibility than the covered portion of the body, so that it can more easily deform to accommodate the curved needle.

The liner, in the collapsed configuration, may be substantially flat and may be a lay-flat tube. The liner, in the collapsed configuration, may have a width and a height, the width being greater than the height. The width may be significantly greater than the height. A ratio of the height to the width may be in the range of from about 1:100 to about 1:10.

The assembly may comprise a flexible connecting component for releasably connecting the threading element to the liner. The flexible connecting component may be formed into a loop which extends from the threading element. The liner may be coupled to the threading element by folding the liner over the loop and coupling a folded part of the liner to a main part of the liner.

The second end of the body may be a trailing end, and the spring may have an open end which defines the second end of the body. The spring may define the internal cavity of the body, the flexible connecting component passing into the open end and along the internal cavity.

The first end of the body may be a leading end, and the spring may have a further open end which defines the first end of the body. The flexible connecting element may extend along the internal cavity to the further open end of the spring, exiting the spring from the further open end and passing away from the open end between the outer surface of the spring and the inner surface of the outer sleeve.

The liner may comprise a sheath lining portion adapted to be located within the lumen of the tendon sheath, and a pulling portion extending from the lumen lining portion and adapted to be used to pull the sheath lining portion into and along the lumen. The sheath lining portion may be substantially tubular, and the pulling portion may comprise one or more leg which extends from the sheath lining portion.

The spring may be generally tubular, and may be a helically wound spring.

A kit may be provided comprising the assembly of the third or sixth aspects of the present disclosure and at least one further liner, which may be of the type defined above.

The further liner may have a use in a tendon repair procedure of a further tendon, for example in the same or in a second (and optionally further) finger.

Reference is made to a 'rest' configuration of the liner. It will be understood that such may be the configuration which the liner adopts in the absence of an external force, such as the force of a tendon stump passing along the internal passage defined by the liner, which may act to expand the liner. Suitable materials for the liner include those discussed elsewhere in this document.

According to a seventh aspect of the present disclosure, there is provided a method of retrieving a tendon stump of a severed tendon, the method comprising the steps of:

providing an elongate threading element having a first end, a second end opposite the first end, and a body extending between the first and second ends and having an internal cavity, the body being deformable into a curved shape, the body optionally comprising a spring having a plurality of coils;

releasably coupling the elongate threading element to a liner defining an internal passage, the liner optionally having a collapsed, rest configuration and an expanded, operating configuration;

inserting the elongate threading element into a lumen of a tendon sheath trailing the liner behind it, optionally with the liner in the collapsed configuration;

directing the elongate threading element along the lumen of the tendon sheath to draw the liner into the lumen, and locating the liner in the tendon sheath so that it can line an internal surface of the tendon sheath;

removing the elongate threading element from the lumen of the tendon sheath and releasing the liner from the threading element leaving the liner in place within the lumen;

passing a curved needle trailing a suture through a first tendon stump, to connect the suture to the first tendon stump;

locating the curved needle within the internal cavity so that the needle is covered by the body and the body deformed to the curved shape by the needle;

inserting the first end of the elongate threading element into the internal passage of the liner, and directing the threading element along the internal passage carrying the needle and the trailing suture towards a second tendon stump spaced along the tendon sheath from the first tendon stump;

drawing the first tendon stump along the internal passage of the liner using the suture to a position proximate the second tendon stump, so that the tendon stumps can be connected, in which the first tendon stump optionally moves the liner to the expanded configuration during movement along the internal passage.

The assembly of the sixth aspect and the method of the seventh aspect of the present disclosure address one or more problems in the prior art, particularly in US-2013/0144310A1. The assembly is easy to put together and speeds a procedure to repair a severed tendon without requiring the complex tendon anchor of US-2013/0144310A1. The curved needle greatly improves the ability to connect sutures to the tendon stumps, and avoids a requirement to use cumbersome clamps to hold the stumps. The threading element, comprising a spring, facilitates passing of the element (trailing the tendon stump) along the lumen of the tendon sheath. The curved needle is contained within the cavity defined by the body of the threading element (within the spring), which can deform to accommodate the needle. This prevents contact between the needle and the tendon sheath and so avoids damage to the tendon sheath during passage along the lumen, and misdirection of the needle. The liner acts to line the internal surface of the tendon sheath, preventing contact between the tendon stump and the internal surface during passage along the lumen. This reduces a risk of fraying of the tendon stump. Also, the use of sleeves and connectors (as described in US-2013/0144310A1), which become embedded in the repaired tendon is avoided, enhancing tissue ingrowth and patient's recovery.

In general terms, the ability to pass a curved needle through the tendon sheath, or through the liner described, greatly improves the procedure of tendon repair in that it obviates the need for multiple suturing of the tendon stump necessary in the usual surgical practice. Using one suture for the repair procedure means less trauma to the tendon stump which would expedite the healing of the tendon repair and in turn the recovery of the patient.

The present method may further comprise removing the elongate threading element from the tendon sheath; removing the needle from the cavity in the body of the elongate threading element; and passing the curved needle trailing the suture through the second tendon stump, to connect the suture to the second tendon stump, so that the first tendon stump can be connected to the second tendon stump.

The present method may further comprise locating a free end of the suture within the cavity defined by the body of the elongate threading element prior to directing the elongate threading element along the lumen of the tendon sheath. The threading element may be partially inserted into the lumen, so that the second end of the body remains exposed from the lumen, and the curved needle then inserted into the cavity defined by the body.

The step of drawing the first tendon stump along the internal passage of the liner may comprise translating the first tendon stump relative to the liner.

The method may comprise removing the liner from the tendon sheath following drawing of the first tendon stump along the internal passage of the liner to the position proximate the second tendon stump.

The elongate threading element may be releasably coupled to the liner via a flexible connecting component extending between the threading element and the liner. The step of releasing the liner from the threading element may comprise severing a portion of the liner that is connected to the flexible connecting component from a remainder of the liner (leaving the liner in place within the lumen), and releasing the flexible connecting component from the threading element.

The assembly of the sixth aspect of the present disclosure effectively comprises a combination of features of the needle covering and carrying device of the first aspect of the present disclosure/assembly of the second aspect of the present disclosure, with the assembly of the third aspect of the present disclosure. Further features of the assembly of the sixth aspect may be derived from the text set out elsewhere in this document, particularly in or with reference to the first, second and/or third aspect of the present disclosure. Similarly, features of the device and assemblies of the first to third aspects may be derived from the text relating to the assembly of the sixth aspect of the present disclosure.

The method of the seventh aspect of the present disclosure effectively comprises a combination of features of the method of the fourth aspect of the present disclosure with the method of the fifth aspect of the present disclosure. Further features of the method of the seventh aspect may be derived from the text set out elsewhere in this document, particularly in or with reference to the fourth, fifth and/or sixth aspects of the present disclosure. Similarly, features of the methods of the fourth and fifth aspects of the present disclosure may be derived from the text relating to the method of the sixth and/or seventh aspect of the present disclosure.

BRIEF DESCRIPTION OF THE DRAWINGS

Embodiments of the present disclosure will now be described, by way of example only, with reference to the accompanying drawings, in which:

FIGS. 10 and 11 are enlarged perspective views of part of the needle covering and carrying device shown in FIG. 9, illustrating insertion of the needle into the device;

FIG. 13 is a view of the hand of the patient which corresponds to that shown in FIG. 2, illustrating steps in a method of lining a tendon sheath, employing an assembly, in accordance with an embodiment of the present disclosure;

FIG. 14 is a side view of a liner which forms part of the assembly shown in FIG. 13;

FIG. 15 is a side view of an alternative liner;

FIG. 18 is a side view of a threading element which forms part of the assembly shown in FIG. 13;

FIG. 19 (presented on the same sheet as FIG. 13) is a perspective view of the liner shown separately from the hand, shown coupled to a flexible connecting element;

FIGS. 20 and 21 are side views of alternative methods of coupling a flexible connecting element of the assembly to the threading element;

FIGS. 22 and 23A are side views of further alternative liners;

FIG. 23B is a view of the liner shown in FIG. 23A, showing a flexible connecting element coupled to the liner;

FIGS. 27 to 30 are views of a hand of a patient which correspond to that shown in FIG. 2, illustrating steps in a method of retrieving a tendon stump of a severed tendon, in accordance with an embodiment of the present disclosure, employing the assembly of FIGS. 25 and 26.

DETAILED DESCRIPTION

Figure 1:
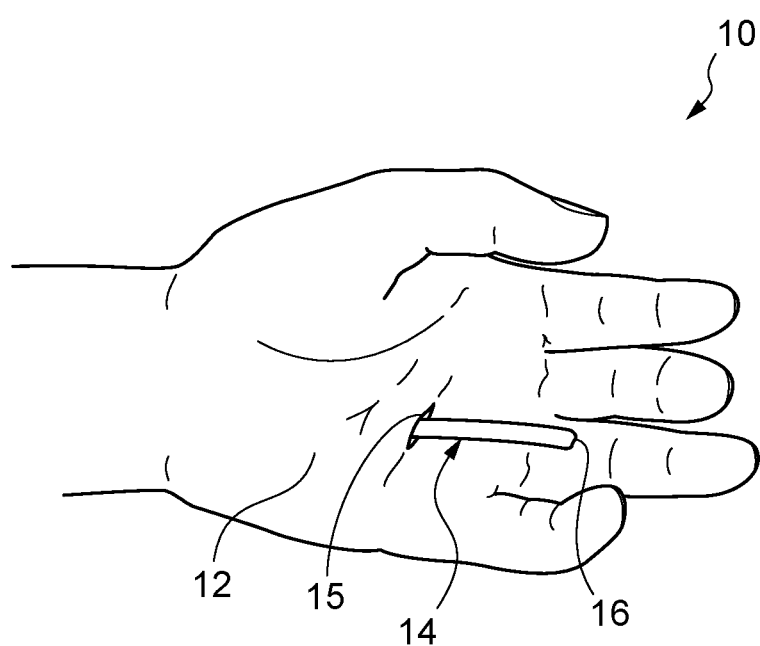
FIG. 1 is a view of a hand of a patient, viewing towards the palm, that has suffered an injury resulting in severing of a flexor digitorum profundus (FDP) tendon in Zone one.
Figure 2:
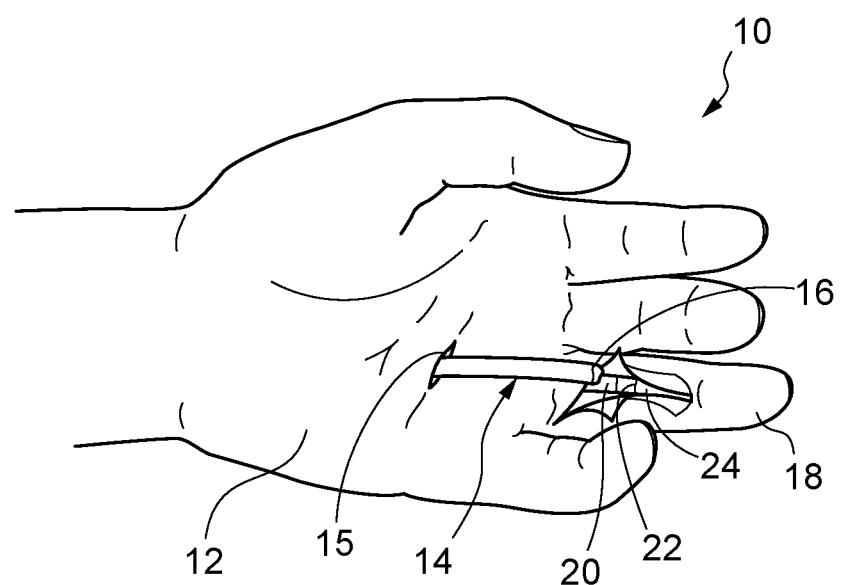
FIG. 2 is a view similar to FIG. 1, showing a finger associated with the tendon opened up to expose a tendon sheath which contains the tendon.

Turning firstly to FIG. 1, there is shown a view of a hand 10 of a patient, viewing towards the palm 12, that has suffered an injury resulting in severing of a flexor digitorum profundus (FDP) tendon 14 in Zone one. Severing of the FDP tendon 14 has resulted in retraction of a proximal portion of the tendon into the palm 12. The drawing illustrates the proximal portion of the tendon 14 retracted outside of the skin through a surgical opening 15, and shows the proximal portion of the tendon having a first stump 16 at the location of the injury. FIG. 2 is a view similar to FIG. 1, showing a finger 18 associated with the tendon 14 surgically opened to expose a tendon sheath 20 which contains the tendon. The drawing also shows a second stump 22 of a distal tendon portion 24 remaining in the finger 18. A surgical procedure to repair the severed tendon 14 involves connecting the first tendon stump 16 to the second tendon stump 22. This restores function to the tendon 14 and so the finger 18, whose flexing movement is controlled by the tendon.

Figure 3:
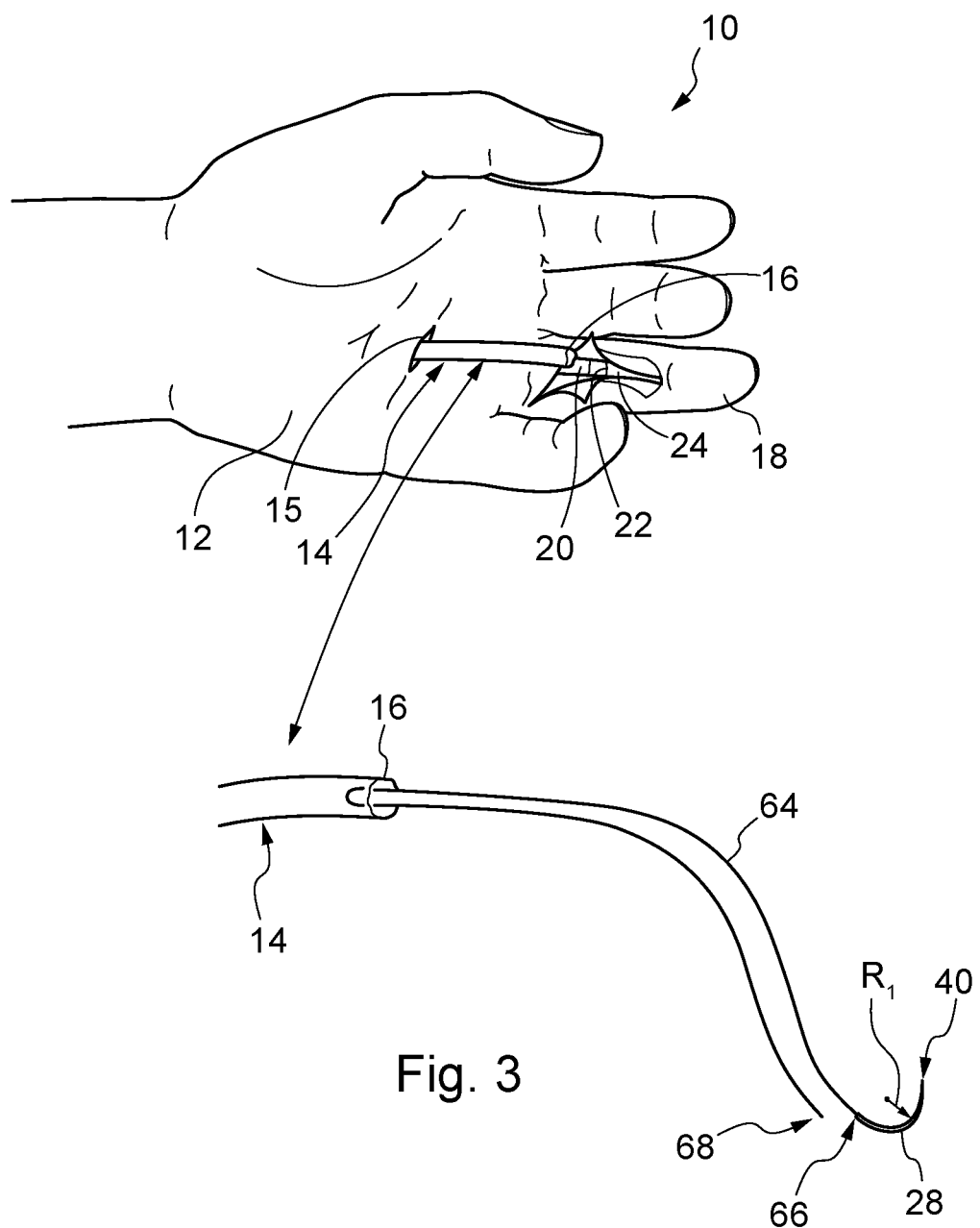
FIG. 3 is a view similar to FIG. 2, showing steps in a method of repairing a severed tendon employing a needle covering and carrying device, in accordance with an embodiment of the present disclosure.
Figure 4:
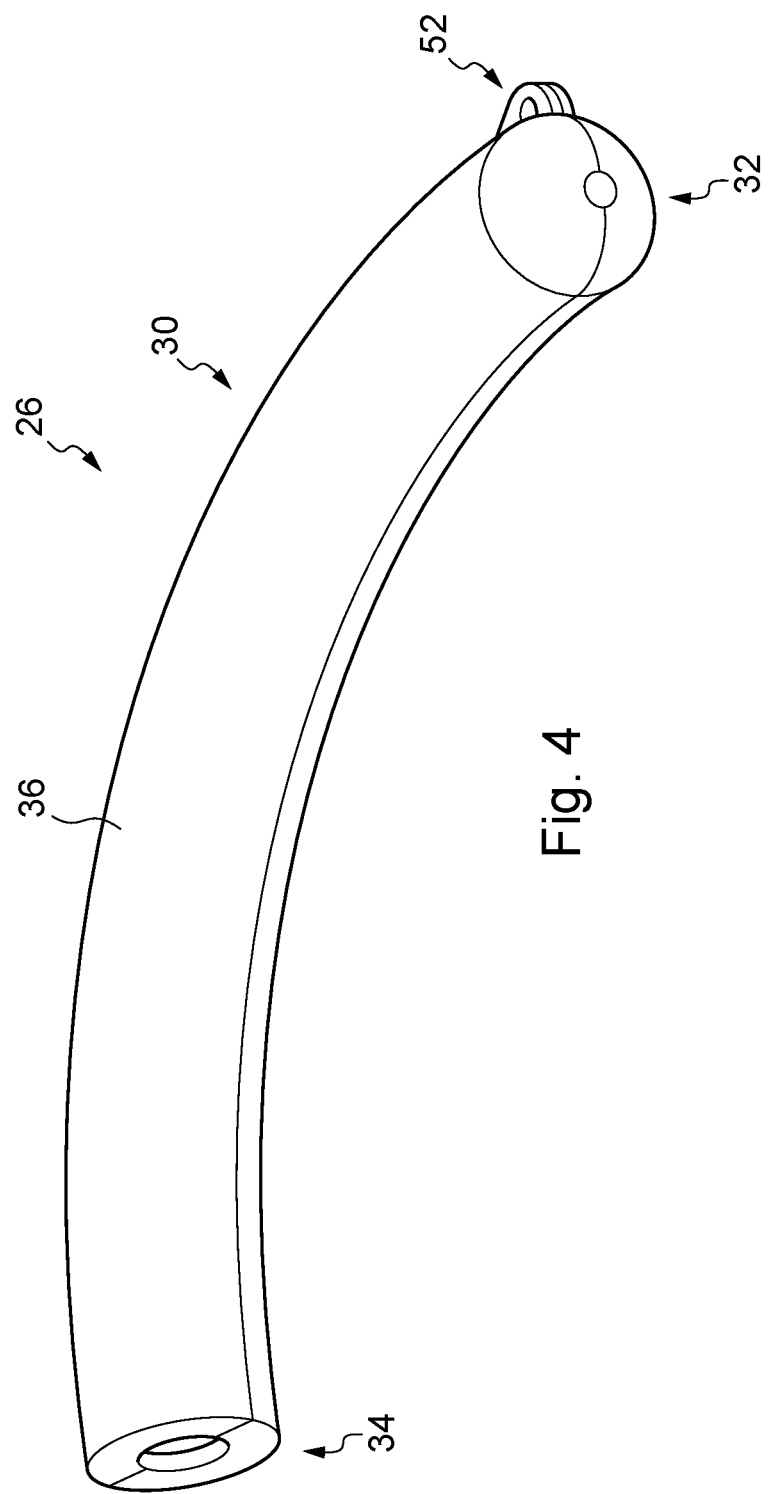
FIGS. 4, 5 and 6 are perspective views, taken from different angles, of a needle covering and carrying device in accordance with an embodiment of the present disclosure.
Figure 5:
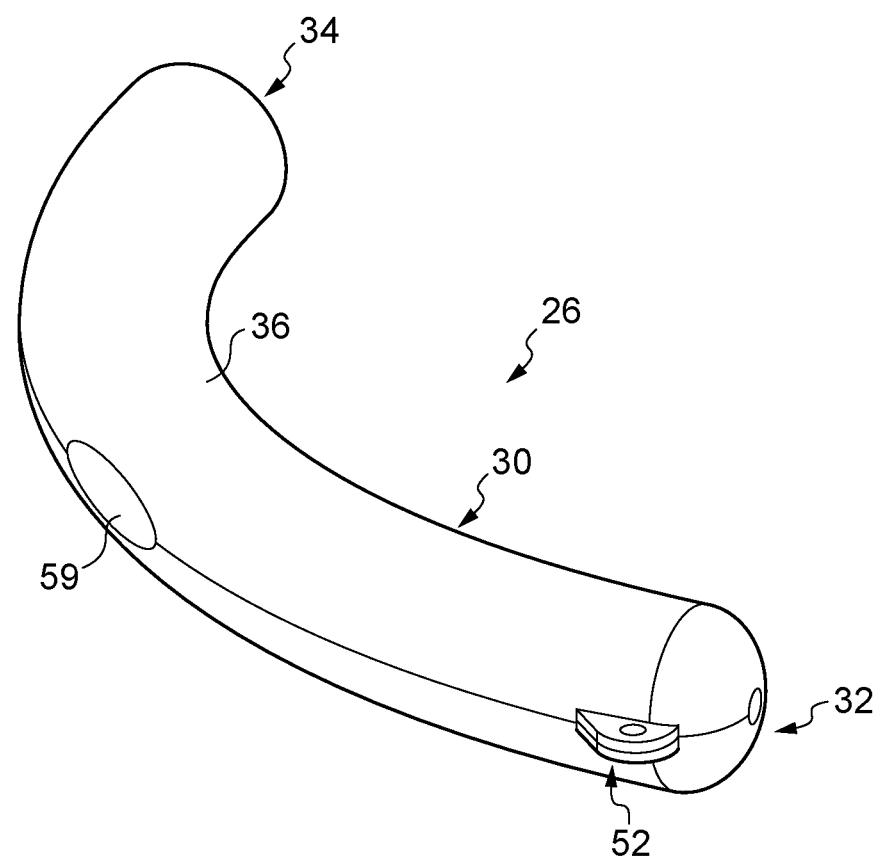
Figure 6:
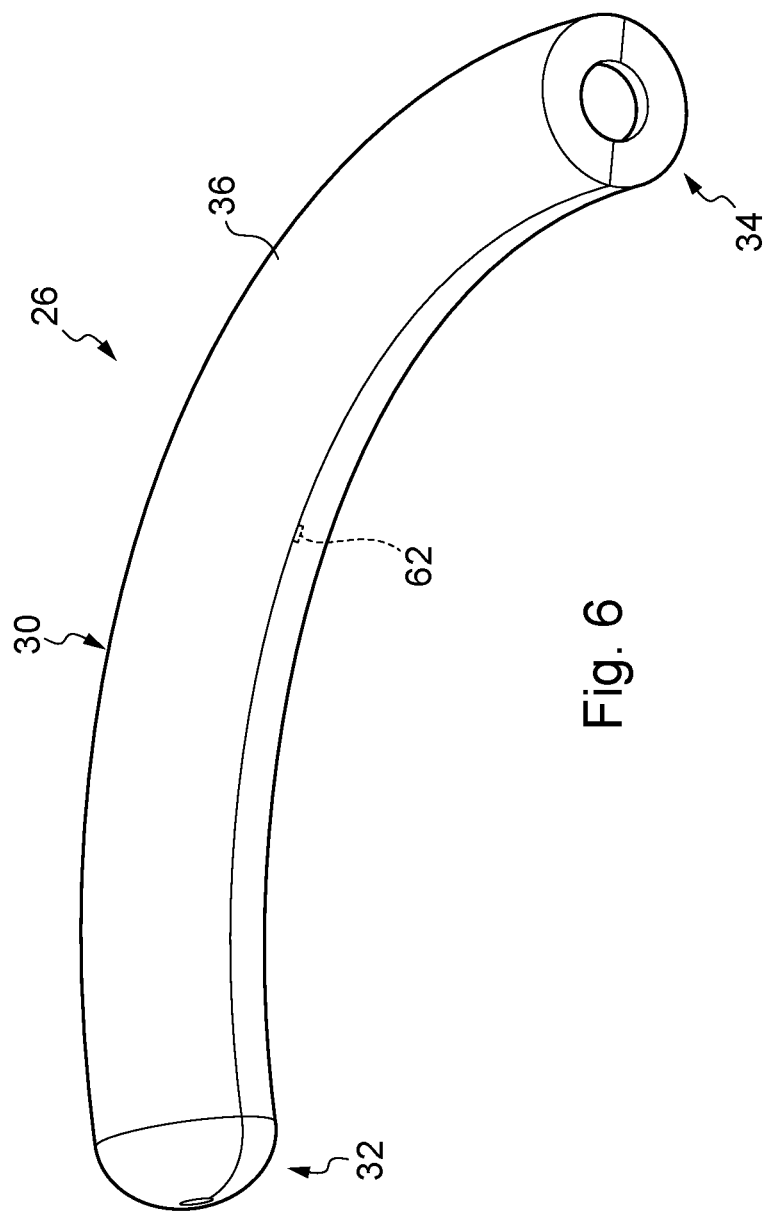

Turning now to FIG. 3, there is shown a view similar to FIG. 2, but showing steps in a method of repairing a severed tendon employing a needle covering and carrying device, in accordance with an embodiment of the present disclosure. The needle covering and carrying device is shown in the perspective view of FIGS. 4, 5 and 6, which are taken from different angles, and is indicated generally by reference numeral 26. The device 26 serves for covering a curved needle 28, which is shown in FIG. 3, as well as for carrying the needle within a lumen of a tendon sheath, in this case the sheath 20 shown in FIGS. 2 and 3.

The device 26 in the illustrated embodiment comprises an elongate element 30 having a first end 32 (which is suitably rounded or tapered), a second end 34 opposite the first end, and a body 36 extending between the first and second ends. In particular embodiments, the body 36 has a generally cylindrical tubular shape, and is generally circular in cross-section. The body 36 can, however, have other shapes, including a rectangular cross section (not shown in the drawing). The body 36 defines an internal cavity 38 for at least partially or entirely accommodating the curved needle 28 so that at least a penetrating tip 40 of the needle is disposed within the body 36, the cavity shown in FIG. 7, which is a perspective view of the body in an open position (which will be discussed in more detail below). This serves to protect the tendon sheath 20 from damage through contact with the needle 28 (particularly the tip 40) during passage of the needle 28 within the sheath.

In the device 26 shown in FIGS. 4 to 7, the body is substantially rigid, and has a curved shape suited to accommodate the curved needle 28. The cavity 38 is shaped to receive the entire needle 28, so that the needle is shrouded or enveloped by the body. The cavity 38 desirably extends from the first end 32 of the device 26 to the second end 34, the first end forming a leading end and the second end a trailing end of the device. In the illustrated embodiment, the first end 32 is closed, and the second end 34 is open and communicates with the cavity 38. In this way, and as will be described below, a suture coupled to the needle 28 can pass out of the cavity 38 and so exit the body 36. However, the open second end 34 may additionally or alternatively facilitate insertion of the needle 28 into the cavity 38, through the open end.

The body 36 serves for transporting the needle 28 within the tendon sheath 20, which is achieved by inserting the first end 32 of the body into the sheath 20 and directing it along the sheath. Transportation of the body 36 along the sheath 20 is achieved using a transportation assembly, as shown in FIG. 8, which is a view similar to FIG. 3, showing a further step in the method employing the device 26. The transportation assembly is indicated generally by reference numeral 42, and comprises an elongate threading element (or threader) 44 and a flexible connecting component 46 connected to the threader. In certain embodiments, the threader 44 suitably takes the form of a rod or wire having a blunt (rounded) end 48 (which facilitates passage along the sheath 20 whilst reducing the risk of damage to the sheath) and an eye or ring 50 (or similar coupling element) for coupling to the connecting component 46. The connecting component 46 in certain embodiments is flexible, and suitably takes the form of a cord, wire, filament or the like, particularly a medical suture. One end of the connecting component 46 can be secured to the eye or ring 50, such as by tying off the end of the connecting component to the eye or ring 50. The body 36 includes a coupling 52 (FIG. 7), which can take the form of, for example, an eye or hoop or ring mounted on or integrally formed as part of the body. The eye 52 serves for connecting the device 26 to the transportation assembly 42, specifically to the connecting component 46 (e.g., a suture), such as by threading the adjacent end of the connecting component 46 through the eye 52 and tying off that end of the connecting component. In this way, and as will be described below, the device 26 can be drawn through the tendon sheath 20 using the transportation device 42, by passing the threader 44 through the sheath trailing the device 26 behind it, which is connected to the threader by the connecting component 46.

Figure 7:
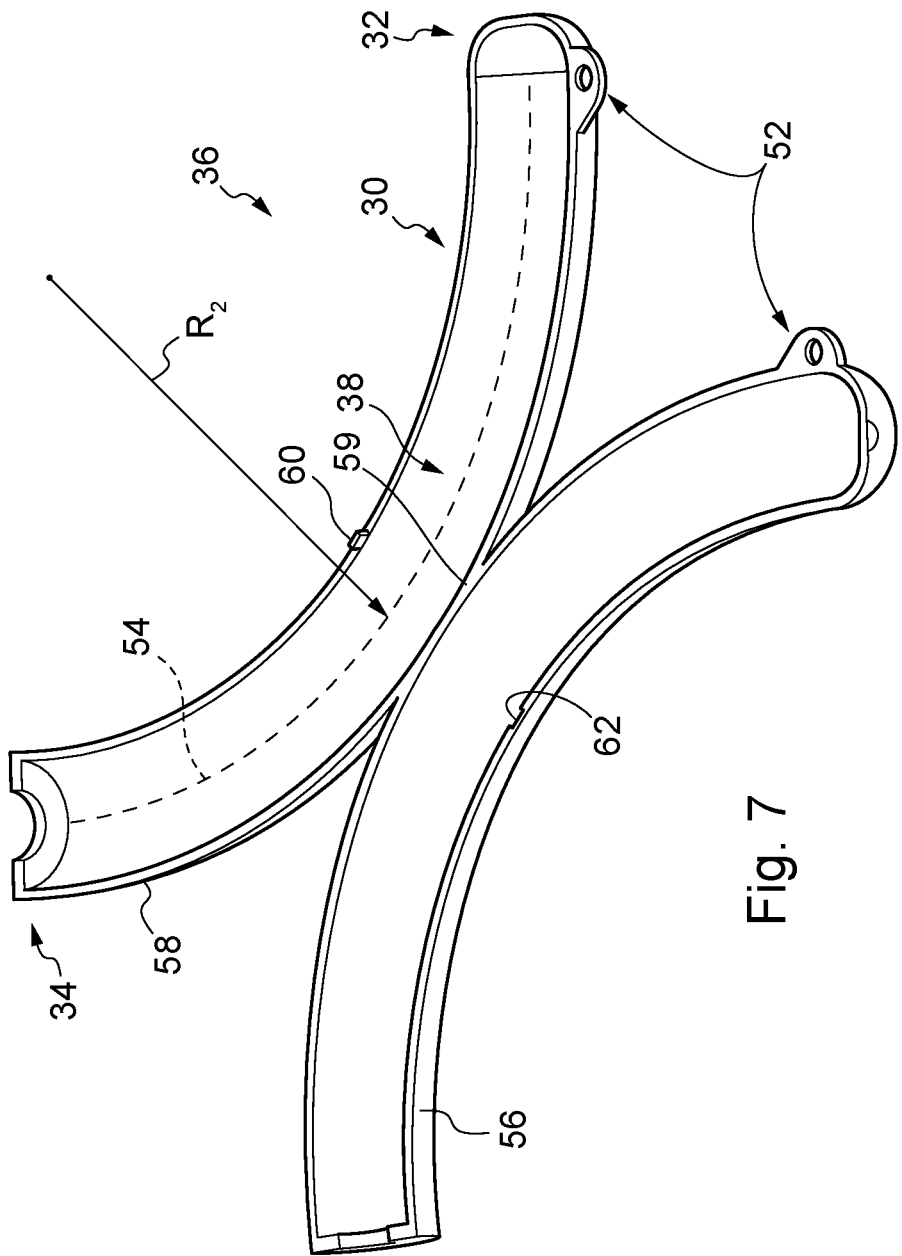
FIG. 7 is a perspective view of the needle covering and carrying device shown in an open configuration.
Figure 8:
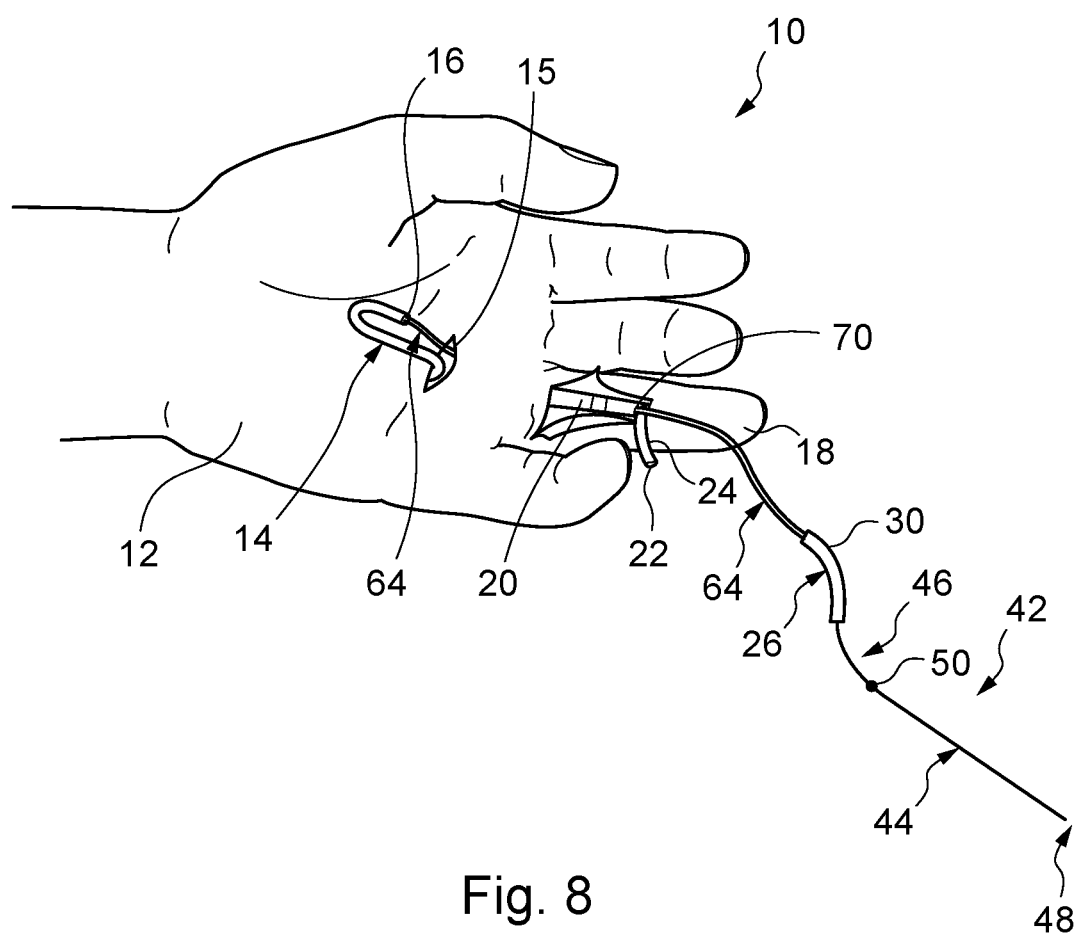
FIG. 8 is a view similar to FIG. 3, showing a further step in the method employing the needle covering and carrying device.

As can be seen from FIG. 7, the cavity 38 is curved, and has a curved shape which substantially matches that of the needle 28. Specifically, the needle 28 has a radius of curvature $R_1$ (FIG. 3), whilst the cavity 38 has a radius of curvature $R_2$ (FIG. 7), which may be taken to a centreline 54 of the cavity. The radius of curvature $R_2$ of the cavity 38 substantially matches the radius of curvature $R_1$ of the needle 28, so that the cavity can comfortably accommodate the needle. However, it will be understood that small differences in these radii will not prevent the needle 28 from being accommodated within the cavity 38.

As shown in FIG. 7, the body 36 in the illustrated embodiment comprises a first body part 56 and a second body part 58, which is pivotably coupled to the first body part. The first and second body parts 56 and 58, when coupled, together form the body 36. The first and second body parts 56 and 58 are pivotable relative to one another between an open position (FIG. 7) in which the needle 28 can be inserted into the cavity 38, and a closed position (FIG. 4) in which the cavity is closed so as to securely contain the needle within the cavity during passage within the lumen of the tendon sheath 20. Pivoting movement of the first and second body parts 56 and 58 relative to the other is facilitated by a hinge 59, which may suitably take the form of a living hinge, coupling the first and second body parts to each other.

The body 36 can be locked in its closed position, by means of a lock comprising a tab 60 on the second body part 58, which engages in a recess 62 in the first body part 56. The tab 60 and recess 62 may lock the body 36 in its closed position by appropriate dimensioning of the tab and recess (e.g. by providing the tab 60 of a length which resists pivoting movement of the parts 54 and 56 relative to one another when the tab is disposed in the recess), and/or by making the tab 60 resilient so that it imparts a restraining force on the part 56 when it is located in the recess 62. The tab 60 can be manually depressed or moved out of engagement with the recess 62 to unlock the lock and permit pivoting of the first and second body parts to the open position. Suitable materials for the body include plastics, particularly polymeric materials, metals and metal alloys.

The method of repairing the tendon 14 employing the device 24 will now be described in more detail.

In a first step, the proximal portion of the tendon 14 is retracted via opening 15 to expose the first stump 16 outside the skin, as shown in FIG. 1. The finger 18 is then laid open by making one or more incisions and peeling back the skin, as show in FIG. 2, and the second tendon stump 22 located. The curved needle 28 is typically supplied with a suture 64 secured to the needle at a first end 66 (such as by crimping the needle around an end portion of the suture), and has a second, free end 68, which is shown in the enlarged detail view in FIG. 3. The needle 28, trailing the suture 64, is then passed through the first tendon stump, as also shown in the enlarged detail view in FIG. 3. In this way, the suture 64 is connected to the first tendon stump 16.

The body 36 of the needle carrying device 26 is then moved to its open position, by pivoting the body parts 54 and 56 relative to one another, towards the open position shown in FIG. 7. The needle 28 is then positioned in a part of the cavity 38 defined by one of the body parts, with the suture 64 trailing from the needle passing out of the body through the open second end 34. The free end 68 of the suture 64 is then also placed within the cavity 38, trailing out of the open second end 34. The suture 64 is thus formed into a loop trailing from the needle 28 and out of the body 36, through the first tendon stump 16 and then back into the body 36. The body 36 can then be closed, retaining the curved needle 28, and the second end 68 of the suture 64, within the cavity 38 defined by the body. In this way, the sharp penetrating tip 40 of the needle 28 in particular is covered by the device 26. In alternative embodiments, the body 36 can include multiple cavities 38, such as one cavity sized to receive the needle 28 and another cavity sized to receive the free end 68 of the suture 64. In other embodiments, the free end 68 of the suture 64 need not be placed inside of the device 26 and instead can be otherwise secure to a location on the outside of the device such that the suture 64 still forms a loop extending from the needle 28.

The blunt end 48 of the threader 44 is then inserted through the opening 15 in the palm 12, and directed into the tendon sheath 20. It will be understood that, in order to withdraw and expose the first tendon stump 14, an aperture (not shown) may need to be formed in the tendon sheath. Typically, the threader 44 will be directed into the tendon sheath 20 through that aperture.

The first end 32 of the device 26, which is connected to the threader 44 by the suture 46, is then fed into tendon sheath 20 through the aperture in the portion of the sheath contained in the palm 18. The threader 44 is then passed through the tendon sheath 20 to the vicinity of the second tendon stump 22, and is directed out of the sheath through another surgically formed aperture 70 (FIG. 8). The threader 44 carries the device 26 through the sheath 20, via the connecting component 46. The threader 44 is then pulled away from the tendon sheath, drawing the device 26 containing the curved needle 28 and the second end 68 of the suture 64 out of the sheath, as shown in FIG. 8.

The second tendon stump 22 is exposed from the finger 18, ready for connection to the first tendon stump 16. The needle 28 and the second end 68 of the suture 64 can then be removed from the cavity 38 in the body 36. The suture 64 is then used to draw the first tendon stump 16 through the tendon sheath 20, which will require suitable manipulation of the stump into the aperture in the portion of the sheath contained in the palm 12. The first tendon stump 16 is drawn along the sheath 20 and out of the aperture 70, so that it is exposed from finger 18 proximate the second tendon stump 22 (which is also exposed ready for connection to the first stump).

The curved needle 28, trailing the suture 64, is then passed through the second tendon stump 22 using a suitable stitching pattern (such as a modified Kessler stitch), to connect the suture to the second tendon stump. The suture 64 and needle 28 are then manipulated to tighten the stitch and securely connect the first tendon stump 16 to the second tendon stump 22, thereby repairing the severed tendon 14, which can be manipulated back into the position within the tendon sheath 20. The operation can then be completed by carrying out any required remediation to the tissue (such as repositioning portions of the tendon sheath, pulleys and the like), and the openings (or incisions) in the palm 12 and finger 18 can then be closed.

Figure 9:
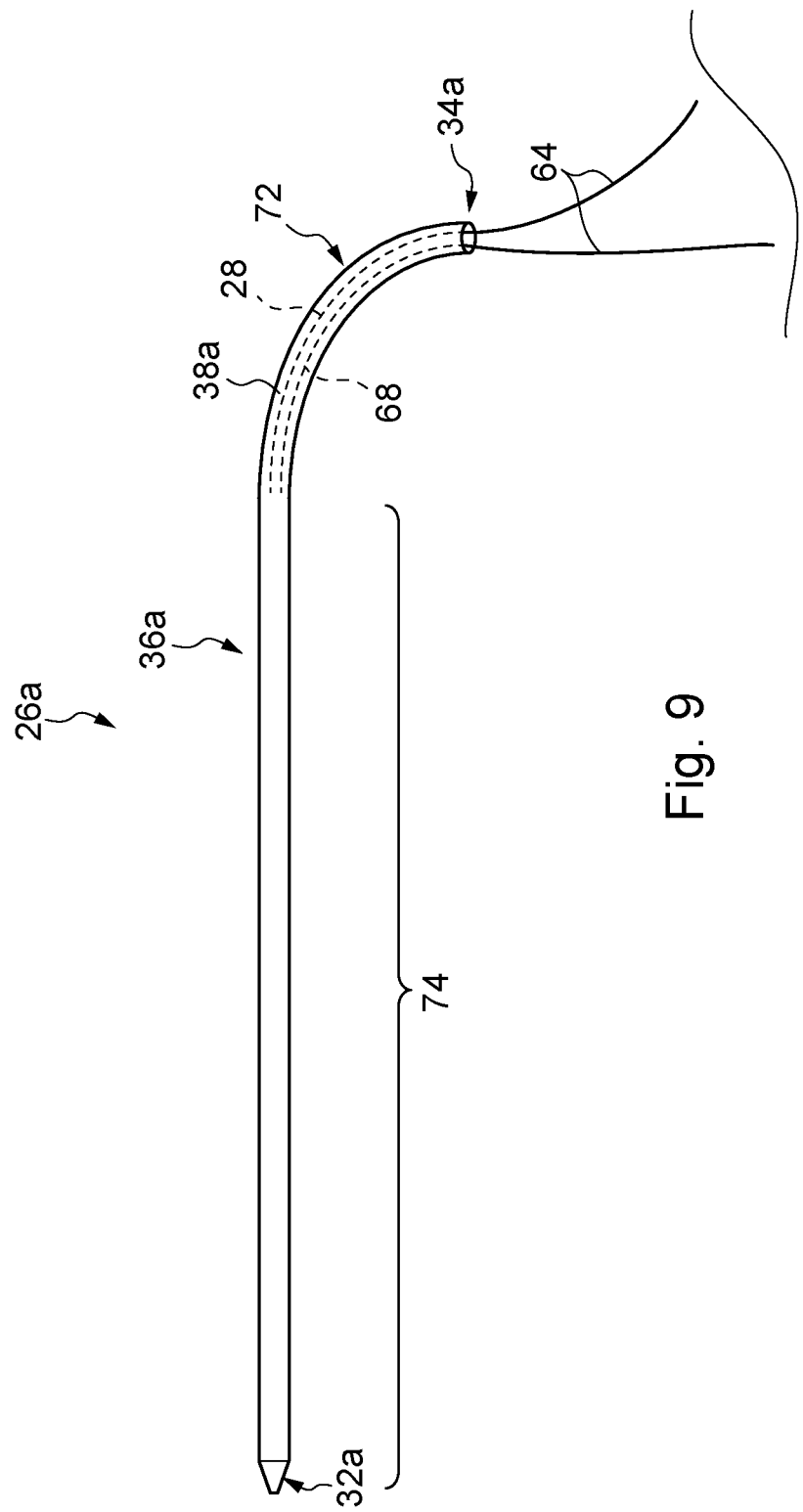
FIG. 9 is a side view of a needle covering and carrying device in accordance with another embodiment of the present disclosure.

Turning now to FIG. 9, there is shown a side view of a needle covering and carrying device in accordance with another embodiment of the present invention, the device indicated generally by reference numeral 26a. Like components of the device 26a shown in FIG. 9 with the device 26 shown in FIGS. 4 to 8 share the same reference numerals with the addition of the suffix 'a'. Only the substantive differences between the device 26a and the device 26 will be described in detail herein.

The device 26a comprises a first end 32a, a second end 34a opposite the first end, and a body 36a extending between the first and second ends. The first end 32a is suitably tapered or rounded, in order to facilitate entry into and passage along the tendon sheath 20. The body 36a defines a cavity or lumen 38a for receiving the curved needle 28 and the trailing end 68 of the suture 64, in the fashion described above in relation to the device 26. In alternative embodiments, the body 36a can have separate cavities or lumens for receiving the needle 28 and the trailing end 68 of the suture, respectively. A part 72 of the body 36a defines the cavity 38a, and is plastically deformable. Optionally however, the entire body 36a can be plastically deformable. The device 26a is therefore capable of being bent into a required shape, to accommodate the curved needle 28, either manually and/or using one or more tools. This may occur either on insertion of the needle 28 into the cavity 38a, or in advance such as by appropriate manipulation of the body to have a shape which suits a particular needle. Suitable plastically deformable materials for forming the portion 72, and optionally the entire body 36a, particularly include metals and metal alloys.

At least the portion 72 of the body 36a, and suitably the entire body, is tubular and may be a generally cylindrical tubular. The needle 28 and trailing end 68 of the suture 64, are both inserted into the cavity 38a through the second end 34a, which is open as shown in FIG. 9. Insertion of the needle 28 and trailing end 68 is illustrated in the enlarged perspective views of FIGS. 10 and 11, which show progressive insertion of these parts in the cavity 38a. Once the needle 28 and trailing end 68 are located in the cavity 38a, the device 26a can be inserted into the tendon sheath as described above in relation to the device 26.

The device 26a can include a coupling, such as the coupling eye 52 of the device 26. However, the device 26a may be capable of being used without a transportation assembly 42. To this end, the body 36a may form a threading element (threader) which is adapted to transit along the tendon sheath 20. The body 36a in the illustrated embodiment therefore comprises a threading portion 74 and the portion 72, which forms a cover for the needle 28. The threading portion 74 desirably is substantially straight, which may facilitate transit along the tendon sheath 20. The cover portion 72 is capable of being deformed into the required curved shape to accommodate the curved needle 28, although it is envisaged that the entire body 36a can be plastically deformable to ease manufacture.

Figure 12:
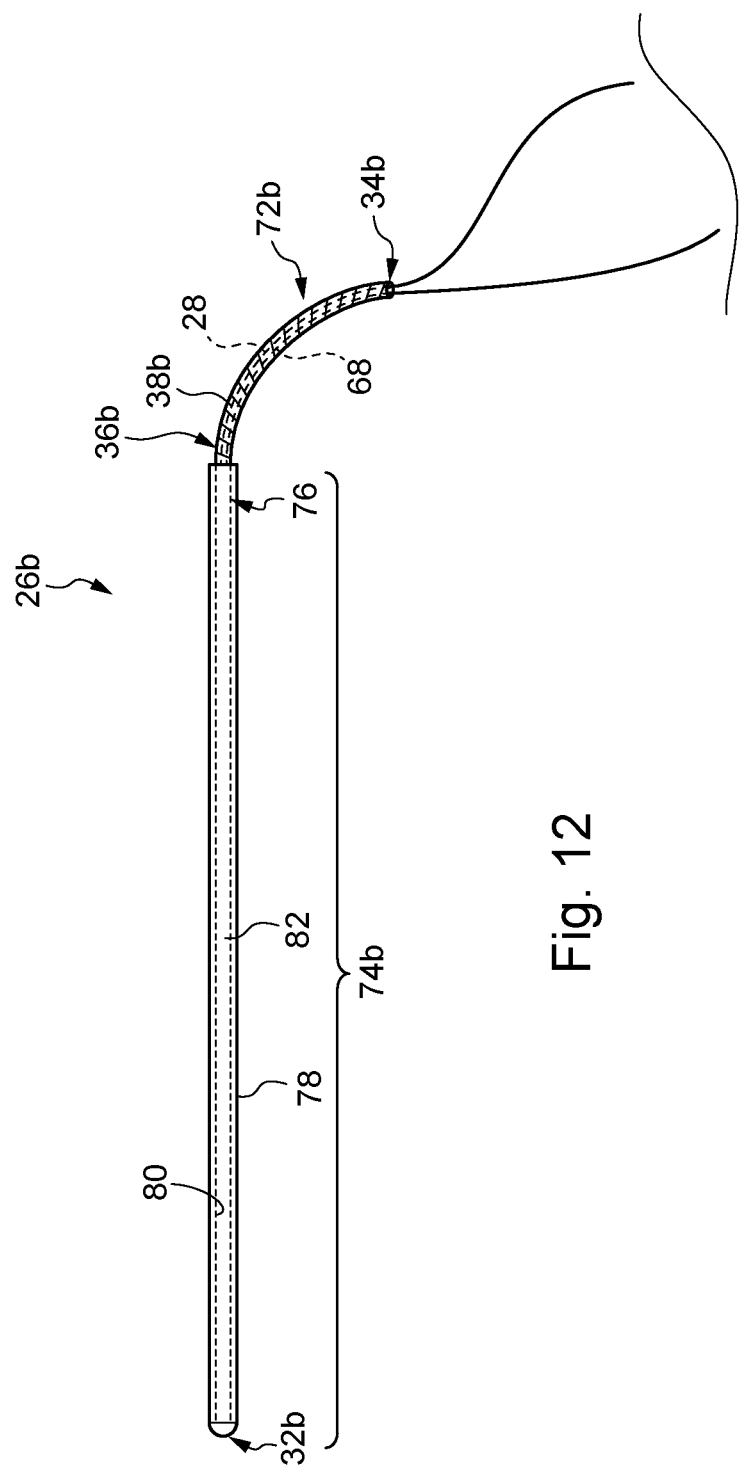
FIG. 12 is a side view of a needle covering and carrying device in accordance with another embodiment of the present disclosure.

Turning now to FIG. 12, there is shown a side view of a needle covering and carrying device in accordance with another embodiment of the present invention, the device indicated generally by reference numeral 26b. Like components of the device 26b shown in FIG. 12 with the device 26 shown in FIGS. 4 to 8, or the device 26a shown in FIGS. 9 to 11, share the same reference numerals with the addition of the suffix 'b', or the suffix 'a' replaced with suffix 'b', as appropriate. Only the substantive differences between the device 26b and the devices 26 and 26a will be described in detail herein.

The device 26b comprises a first end 32b, a second end 34b opposite the first end, and a body 36b extending between the first and second ends. The first end 32b is again tapered or rounded, to facilitate entry into and passage along the tendon sheath 20. The body 36b defines a cavity 38b (or multiple cavities) for receiving the curved needle 28 and the trailing end 68 of the suture 64, in the fashion described above in relation to the device 26. A part 72b of the body 36b defines the cavity 38b, and is elastically deformable. Optionally however, the entire body 36b can be elastically deformable. The device 26b is therefore capable of adopting a curved shape when the needle 28 is inserted into the cavity 38b.

The portion 72b (and optionally the entire body 36b) is elastically deformable from an undeformed or starting configuration, which may be a substantially straight and/or unstressed configuration, to a deformed or deployed configuration shown in FIG. 12, which is a curved configuration. The portion 72b will return to the undeformed configuration when the needle 28 is removed from the cavity 38b. Suitable materials for forming the portion 72b, and suitably the entire body 36b, include metals and metal alloys.

In particular embodiments, the portion 72b, and suitably the entire body 36b, takes the form of a spring, in particular a helically wound tension spring, comprising a plurality of turns or coils 76. The coils 76 are typically arranged so they are in close abutment, at least in a rest state, which may resist entry of tissue in between the coils. In alternative embodiments, the body 36b, or just the portion 72b, can comprise an elastically deformable polymeric tube (e.g., medical grade silicone tubing) or a tube formed from a shape memory metal (e.g., Nitinol), which can be formed with axial and/or circumferential slots to facilitate bending of the tube.

The device 26b also comprises an outer sheath, sleeve or covering 78, which eases passage of the device within the tendon sheath 20. The outer sheath 78 may be of a plastics (suitably polymeric; e.g., a layer of a heat shrink polymer)

or elastomeric material, which materials may have a low coefficient of friction, to facilitate passage of the device along the tendon sheath 20. The outer sheath 78 has an inner surface 80 which is disposed in contact with an outer surface 82 of the body 36b, in particular the spring. In this way, the coils 76 of the spring are covered to resist tissue entry. The outer sheath 78 is tubular, and extends part way along a length of the spring 36b. The outer sheath 78 extends in a direction from the first, leading end 32b towards the second, trailing end 34b. The outer sheath 78 stops short of the portion 72b defining the cavity 38b, so that the second end 34b is exposed. This is desirable because it ensures that the outer sheath 78 does not restrict the elastic deformation of the portion 72b, which is required in order to accommodate the curved needle 28. It will be understood, however, that in a variation on the illustrated embodiment, the outer sheath may extend the full length of the spring 36b, or indeed a shorter distance to that shown, so that it covers just the leading end 32b and a small adjacent part of the spring. Typically, the threading element 26b will have a length in the region of 150 mm, around 85 to 100 mm of which will be covered by the outer sheath 78. The remainder (which forms the portion 72b), around 50 to 65 mm in length, is uncovered so as to ease deformation of the portion to accommodate the curved needle 28.

In use, the device 26b may be drawn along the tendon sheath 20 using a transportation assembly such as the assembly 42, or can form a threader 74b, as described in relation to the device 26a. The outer sheath 78 may act to stiffen the device to resist elastic deformation during transit along the tendon sheath 20, as well as easing passage by resisting entry of tissue into the spring coils and providing a low friction outer skin.

Turning now to FIG. 13, there is shown a view of the hand 10 of the patient as shown in FIG. 2, illustrating steps in a method of lining a tendon sheath, employing an assembly, in accordance with an embodiment of the present disclosure. The method of lining the tendon sheath may also form a preparatory step to the method of repairing a severed tendon shown in FIGS. 1 to 12 and described above.

In the illustrated embodiment, the assembly comprises a threading element 26b which is adapted to transit along a lumen 84 of the tendon sheath 20. In this embodiment, the threading element 26b is provided by the needle covering and carrying device shown in FIG. 12 and described above, and so is indicated by the same reference numeral. It will be understood that further features of the threading element 26b are outlined above. Other threading elements, including the threading element 26a shown in FIG. 9, may be employed. Equally, the method may make use of the assembly shown and described in FIGS. 1 to 8.

The assembly also comprises a liner 86 for lining an internal surface 88 of the tendon sheath 20, the liner defining an internal passage 90 along which a tendon stump can pass during transit along the lumen 84. The liner 86 acts to prevent contact between the tendon stump and the internal surface 88 of the tendon sheath 20. The liner 86 is shown separately in FIG. 14, whilst FIG. 15 shows an alternative embodiment of liner indicated generally by reference numeral 86c. The liners 86 and 86c will be discussed in more detail below.

Figure 16:
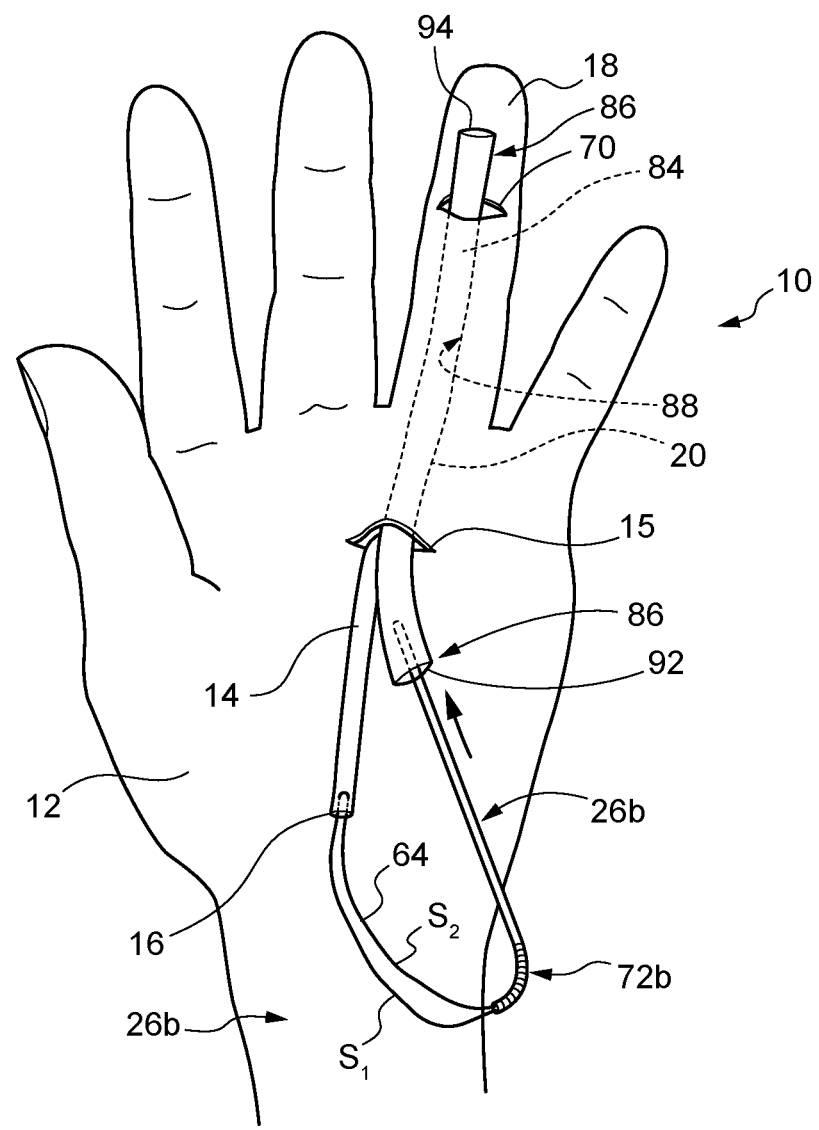
FIGS. 16 and 17 are views of the hand shown in FIG. 13, illustrating further steps in the method.

The liner 86 is adapted to be releasably coupled to the threading element 26b so that it can be drawn into the tendon sheath 20 by the threading element and located within the lumen 84, and then released from the threading element so as to reside within the lumen. FIG. 16 shows the liner 86 following location within the lumen 84 of the tendon sheath 20, the liner 86 protruding at one end from the opening 15 in the palm 12, and at the other end from the aperture 70 in the finger 18. The liner 86 is therefore of a length which is selected so that the liner can pass along the entire length of tendon sheath extending between the opening 15 and the aperture 70, with first and second open ends 92 and 94 of the liner 86 exposed respectively from the palm 12 and the finger 18.

Location of the liner 86 within the lumen 84, so that it lines the internal surface 88 of the tendon sheath 20, provides the advantage that the liner restricts, and potentially completely avoids, damage to the first stump 16 of the tendon 14 when it is drawn along the tendon sheath 20 in the repair procedure described above and shown in FIGS. 1 to 12. This reduces a likelihood of the tendon stump 16 fraying due to contact and snagging with the internal surface 88 of the tendon sheath 20, which could otherwise hamper the repair procedure by making it difficult to suture the first tendon stump 16 to the second tendon stump 22 exposed from the finger 18. Additionally however, the liner 86 restricts contact between other objects and the internal surface 88 of the tendon sheath 20, including but not restricted to the threader 26b itself, when the threader is passed back along the lumen 84 of the tendon sheath 20 in the repair procedure, as will now be described with reference also to FIG. 17, which shows a further step in the repair method.

The assembly further comprises a flexible connecting component for releasably connecting the threading element 26b to the liner 86, the connecting component shown in FIG. 13 and given the reference numeral 96. The connecting component 96 typically takes the form of a medical suture, but may comprise any suitable cord, wire, filament or the like. The suture 96 can be secured to the threading element 26b, such as by whipping the suture around the threading element, as shown in the enlarged view of FIG. 18, the whipping indicated at 98 in the drawing. This secures the suture 96 against movement along a length of the threading element 26b when it is drawn along the lumen 84 of the tendon sheath 20, trailing the liner 86.

The suture 96 can be formed into a loop and can also be connected to the liner 86, such as by whipping, as shown in the detail view of FIG. 19, the whipping illustrated by numeral 100. The whipping 100 desirably is secured around the liner 86 at a location which is spaced from the first open end 92. The part of the liner 86 extending between the open end 92 and the whipping 100 can then be folded back on itself to the position shown in FIG. 13. This provides the advantage that the open end 92 is folded back on itself, smoothing passage of the liner 86 along the lumen 84 and restricting contact between edge surfaces of the liner 86 at the open end 92, by facing the edge surfaces away from the direction of transit.

The liner 86 in the illustrated embodiment is elongate and generally tubular, taking the form of a sheath, as shown in FIG. 14. Whilst the liner 86 is shown as being tubular and generally circular in cross-section, it will be understood that it may have any suitable cross-sectional shape. The liner 86 desirably is formed so as to be collapsible, or adapted to be flattened, for easy insertion into and transit along the lumen 84. This is achieved by selection of suitable flexible materials for the liner, which include polymeric and elastomeric materials, and/or by providing the liner with a wall thickness which is suitable for promoting collapsing/flattening. Suitable wall thicknesses may be of the order of fractions of a millimetre.

Following connection of the threading element 26b to the liner 86 using the suture 96, the leading end 32b of the threading element 26b can be inserted into the lumen 84 at the aperture 70 in the finger 18. The threading element 26b can then be pushed along the lumen 84 until the leading end 32b protrudes from the opening 15 in the palm 12. The threading element 26b can suitably be of a length which is such that the threading element spans the entire length of the tendon sheath 20 extending between the opening 15 and the aperture 70. Accordingly, the trailing end 34b of the threading element 26b will protrude from the opening 70 in the finger 18 after the leading end 32b has exited the lumen 84 through the opening 15 in the palm 12. This enables the threading element 26b to be drawn out of the tendon sheath 20 by grasping the leading end 32b and pulling the threading element.

Transit of the threading element 26b along the lumen 84 of the tendon sheath 20 acts to move the liner 86 towards the opening 70 in the finger 18, due to its connection to the threading element via the suture 96. To position the liner 86 within the tendon sheath 20, the surgeon can grasp the portion of the suture 96 which has been exposed at the palm 12 and pull on the suture in order to draw the liner 86 into the opening 70, suitably using medical pliers or forceps to hold the folded portion of the liner down, and to manipulate the folded portion into the lumen 84 at the opening 70. The surgeon can then pull on the suture 96 to advance the liner 86 into the position shown in FIG. 16, where it spans the opening 15 and aperture 70 as described above.

The threading element 26b can then be released from the liner 86, suitably by cutting the suture 96 and removing any portions of the suture coupled to the threading element 26b. Additionally, the surgeon can cut the liner 86 at a position which is spaced further away from the open first end 92 then the whipping 100, so as to remove the folded and whipped portion, thereby reopening the liner 86. However, alternatively, the whipping 100 can be removed so as to reopen the liner 86.

The surgeon can then secure the suture 64 to the tendon stump 16 using the curved needle 28 (not shown in FIG. 16), and position the curved needle and the second free end 68 of the suture 64 within the deformable part 72b of the threading element 26b. Positioning the curved needle 28 within the deformable part 72b causes the deformable part to adopt the deformed position shown in FIG. 16. The threading element 26b can then be inserted back into the lumen 84, by passing the leading end 32b into the open end 92 of the liner 86, and the threading element can be passed along the internal passage 90 defined by the liner. The threading element 26b transits along the tendon sheath 20 pulling the suture 64, exiting the sheath at the aperture 70 in the finger 18. As discussed above, the liner 86 lines the internal surface 88 of the tendon sheath 20, to prevent contact between the threading element 26b and the sheath surface.

Figure 17:
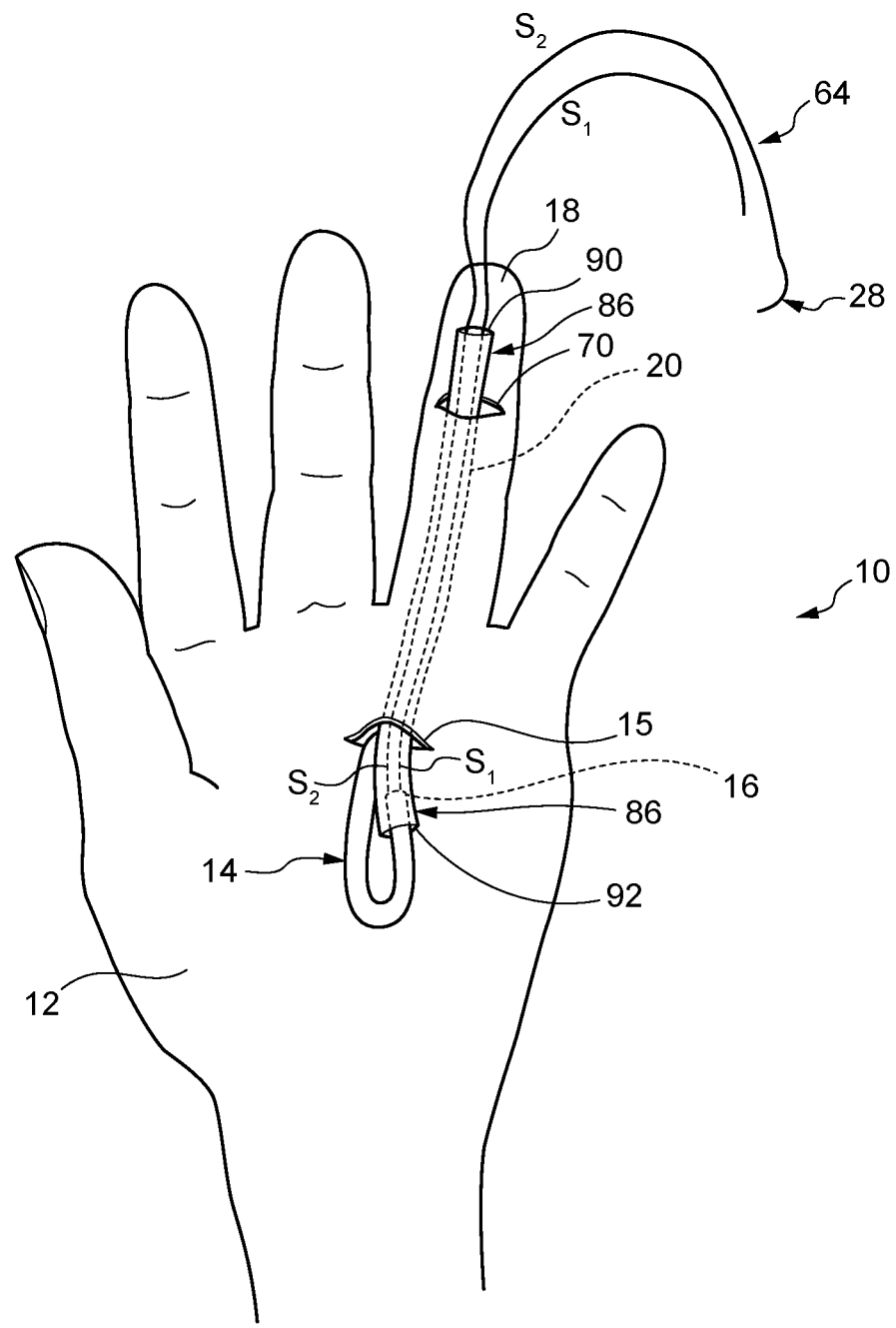

The curved needle 28 and the free end 68 of the suture 64 can then be removed from the deformable part 72b of the threading element 26b, as shown in FIG. 17. The suture 64 can then be used to draw the first tendon stump 16 into the internal passage 90 defined by the liner 82, by manipulating the tendon stump into the liner opening 92, as shown in the drawing. The first tendon stump 16 is then drawn along the tendon sheath 20, the liner 86 similarly serving to restrict contact between the tendon stump 16 and the sheath surface 88. This continues until the first tendon stump 16 emerges from the opening 70 in the finger 18. The liner 86 can then be withdrawn from the lumen 84 of the tendon sheath 20, by sliding the liner over the outer surface of the portion of the tendon located in the lumen, and over the suture 64 and needle 28. The tendon stumps 16 and 22 can then be sutured together to restore function to the tendon 14, following the procedure discussed in detail above. In a variation, the liner 86 may remain in the lumen 84 until after the stumps 16 and 22 have been sutured, and is then removed by pulling on the liner and cutting it as it is exposed from the aperture 70.

Removal of the liner from the lumen 84 can be facilitated by employing the liner 86c shown in FIG. 15. Like components of the liner 86c with the liner 86 of FIG. 14 share the same reference numerals with the addition of the suffix 'c'. The liner 86c includes a slit 102 which extends along an entire length of the liner from its first end 92c to its second end 94c. The liner 86c can be rolled or coiled about its longitudinal axis into the shape of a tube, so as to define an internal passage 90c. The liner 86c can be rolled into the tube shape by arranging a first longitudinal edge 104 so that it overlaps a second longitudinal edge 106. The provision of a liner 86c having such a slit 102 facilitates removal of the liner from the lumen 84 after completion of the tendon repair procedure, in which tendon stumps 16 and 20 are connected, because the slit 102 enables the liner 86c to be drawn over the repaired tendon leaving the tendon in place within the lumen 84. In alternative embodiments, the liner 86c need not be rolled or coiled, and instead the first longitudinal edge 104 can abut or be in close proximity to the second longitudinal edge 106.

Variations on the method of coupling the suture 96 to the threading element 26b are shown in FIGS. 18, 20 and 21. In FIG. 18, the suture is whipped and securely knotted on the external surface of the sheath covering the threading element. In FIG. 20, the suture 96 is whipped directly to the outer surface 82 of the spring 36b, and the sheath 78 located over the whipping 98 to trap the suture between the outer surface 82 and the inner surface 80 of the sheath 78. For example, at least a portion of the suture 96 extending along or around the spring 36b can be captured between the spring and the sheath 78 when the sheath is formed from a layer of a heat shrink polymer around the spring. In FIG. 21, the suture 96 ends 108 and 110 are inserted through an internal passage 112 defined by the spring 36b and through an open end 114 of the spring, and then passed away from the open end along the outer surface 82 of the spring. The sheath 78 is then located over the suture ends 108 and 110, trapping them between the outer surface 82 of the spring 36b and the inner surface 80 of the sheath 78. In a variation on the option shown in FIG. 20, ends of the suture 96 can be positioned along the outer surface 82 of the spring 36b (without being whipped to the spring) and are trapped by the sheath 78. In a variation on the option shown in FIG. 21, the suture ends 108 and 110 may also be whipped to the spring 36b, after exiting the open end 114. Further variations can be envisaged based on combinations of the options discussed above.

In the method described above, the same threading element 26b is used to position the liner 86 within the tendon sheath and to thread the needle and the suture 64 through the liner 86. However, in alternative embodiments, two threading elements 26b can be used to perform these two steps. Moreover, in still alternative embodiments, a different type of threading element can be used to position the liner 86 within the tendon sheath than is used to thread the needle and the suture through the liner. For example, the threading element used to position the liner 86 within the tendon sheath need not have a curved portion or a portion that is deformable to form a curved shape when a needle is inserted into the threaded element. Thus, the threading element used to position the liner 86 within the tendon sheath can comprise an elongated body (e.g., a tubular body) and a connecting component (e.g., a suture or wire, such as in the form of a loop) connected to the elongated body, wherein the connecting component is configured to be releasably coupled to a liner as described herein.

FIG. 22, and FIGS. 23A/B and 24 show alternative liners 86d and 86e. Like components of the liners 86d and 86e with the liner 86 shown in FIGS. 13 to 17 and described above share the same reference numerals, with the addition of the suffixes 'd' and 'e', respectively.

The liner 86d comprises a sheath lining portion 116 adapted to be located within the lumen 84 for lining the tendon sheath 20, and a pulling portion 118 extending from the lumen lining portion. The pulling portion 118 can be used to pull the sheath lining portion 116 into and along the lumen 84 before being severed, leaving the lining portion within the lumen. The pulling portion 118 can have a length which is greater than, or substantially equal to, a length of the sheath lining portion 116. The threading element 26b can be coupled to the pulling portion 118, such as using the connecting component 96 as described above, and used to draw the pulling portion into the lumen 84 in the fashion described above. The pulling portion 118 is then used to draw the sheath lining portion 116 into the lumen 84, by pulling an end 120 of the pulling portion 118 out of the lumen 84. The pulling portion 118 can be gripped by a surgeon and used to pull the sheath lining portion 116 into the lumen 84. The sheath lining portion 116 can be substantially tubular, and the pulling portion 118 can comprise one or more elongate strips, legs or the like, which extend from the tubular lumen lining portion, and which can be provided integrally with the lining portion. In certain embodiments, the liner 86d can be coupled to the threading element 26b by inserting the liner 86d partially into the loop formed by the connecting component 96 and folding the portion 118 over the loop against the portion 116, such as at a location on or adjacent a tapered transition section 122 between portions 116, 118.

The pulling portion 118 can be of reduced width $W_P$ in comparison to a width $W_L$ of the lining portion 116e, which may facilitate insertion of the liner 86d into the lumen 84 of the tendon sheath 20, and transit of the liner along the lumen. This is typically achieved by cutting away sections 119 and 121 of the tubular structure of the liner 86d. Optionally, edges of the legs forming the pulling portion 118 can be sealed together, for example by preforming the cutting procedure using a hot knife. Sealing the edges may further facilitate insertion of the liner 86d into the lumen 84, and transit along the tendon sheath. Sealing the edges of the legs in this way may close the liner 86d in the region of the pulling portion 118. However, it will be understood that the pulling portion 118 can subsequently be cut away, to reopen the liner passage 90 (so that it can received the tendon stump 16 and threading element 26b).

FIG. 23A shows the liner 86e, which is a variation on the liner 86d in which a length of a pulling portion 118e is less than a length of a sheath lining portion 116e. FIG. 23B shows the suture 96 coupled to the liner 86e, optionally by folding over a part of the liner including an open end 92e, and securing the folded part using whipping 124 and 126 which passes around the folded portion. The liner 86e is folded in the region of the pulling portion 118e, which maintains the reduced width ($W_P$ in FIG. 22) at the end of the liner 86e, facilitating insertion into, and transit along, the lumen 84 of the tendon sheath 20. It will be understood that other coupling methods may be employed, which may not involve folding of the liner 86e in this way.

Figure 24A:
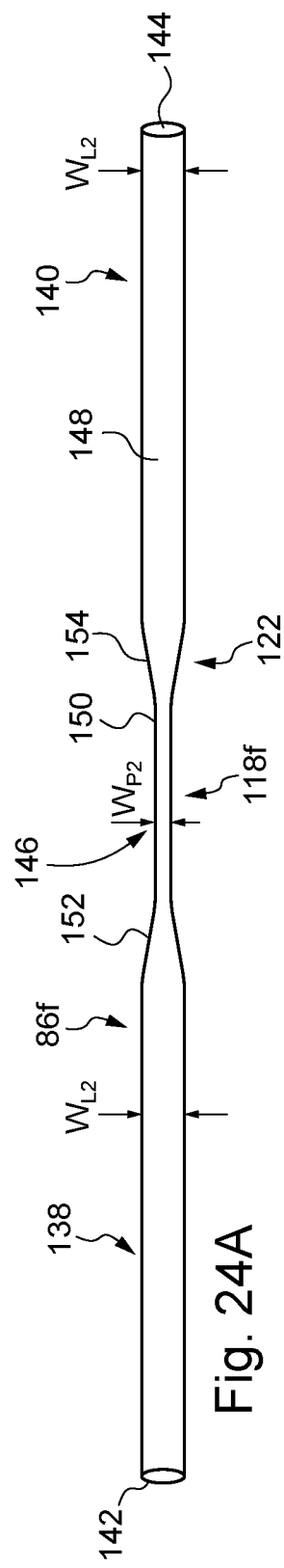
FIG. 24A is a side view of a further alternative liner.
Figure 24B:
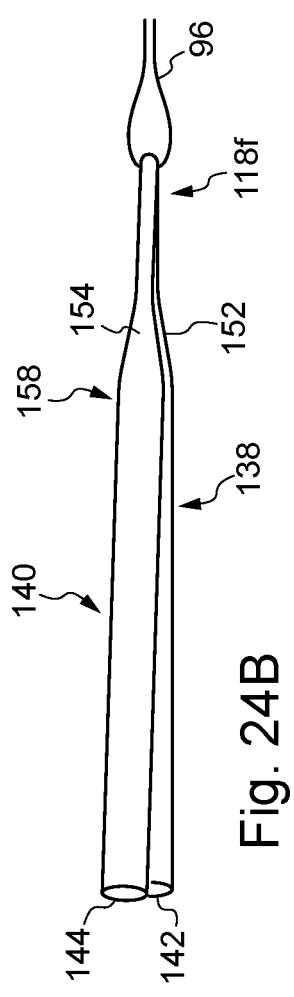
FIG. 24B is a view of the liner shown in FIG. 24A, showing a flexible connecting element coupled to the liner.

FIGS. 24A and 24B show an alternative liner, which may have a use in the repair of two severed tendons. The liner is indicated by reference numeral 86f. Like components of the liner 86f with the liner 86 shown in FIGS. 13 to 17 and described above share the same reference numerals, with the addition of the suffix 'f'.

The liner 86f can be coupled to a connecting component 96 of a threading element (e.g., the threading element 26b) so as to define two tendon sheath lining portions 138 and 140. The liner 86f has a first end 142 and a second end 144, and coupling is achieved by connecting the liner to the connecting component 96 at a point 146 along a length of the liner between the first and second ends, suitably at or proximate a midpoint of the liner. A length of each tendon sheath lining portion 138 and 140 is substantially the same, although the lengths could be different, provided that they are sufficiently long to line the tendon sheath 20 (or at least the part of the tendon sheath extending between the surgical openings 15 and 70). The tendon sheath lining portions 138 and 140 serve for receiving the tendon stumps of respective tendons, which are normally located in the tendon sheath 20. It is well known that the tendon sheath 20 in the finger 18 accommodate more than one tendon. The assembly comprising the liner 86f can therefore enable the two tendon sheath lining portions 138 and 140 to be located in the tendon sheath 20, for use where both of the finger tendons are to be repaired.

The liner 86f also comprises a body 148 extending between the first and second ends 142 and 144. The first tendon sheath lining portion 138 extends from the first end 142 towards a part 118f of the liner disposed between the first and second ends, and which will form a pulling portion. The second tendon sheath lining portion 140 extends from the second end 144 towards the part 118f. The first and second tendon sheath lining portions 138 and 140 each have a width $W_{L2}$, and the part 118f has a width $W_{P2}$ which is less than the width of the first and second tendon sheath lining portions. The width of the first tendon sheath lining portion 138 is suitably the same as (or substantially the same as) the width of the second tendon sheath lining portion 140.

Although less desirable, in alternative embodiments, the liner 86f can have constant width of a substantially constant width from the first end 142 to the second end 144.

The part 118f comprises a main section 150 of substantially constant width, a first transition section 152 extending between the main section 150 and the first tendon sheath lining portion 138, and a second transition section 154 extending between the main section 150 and the second tendon sheath lining portion 140. The transition sections 152 and 154 have a width which progressively increases from the width $W_{P2}$ of the main section 150 to the width $W_{L2}$ of the respective tendon sheath lining portion 138, 140. Typically, this will be achieved by cutting away sections of the tubular structure of the liner 86f, as described above.

The liner 86f is adapted to be releasably coupled to the threading element 26b, in particular the flexible connecting component 96, in the part 118f. Where the flexible connecting component 96 is formed into a loop, the liner 86f is releasably coupled to the threading element by folding it over the loop at the part 118f. The liner 86f is then drawn into the tendon sheath 20 as described above. The first and second tendon sheath lining portions 138 and 140 can then be separated from one another, suitably by severing the liner 86f. This may be achieved by removing the portion 118f, for example by cutting the liner at the location 158, to the left of the transition portions 152 and 154 in FIG. 24B.

Figure 24C:
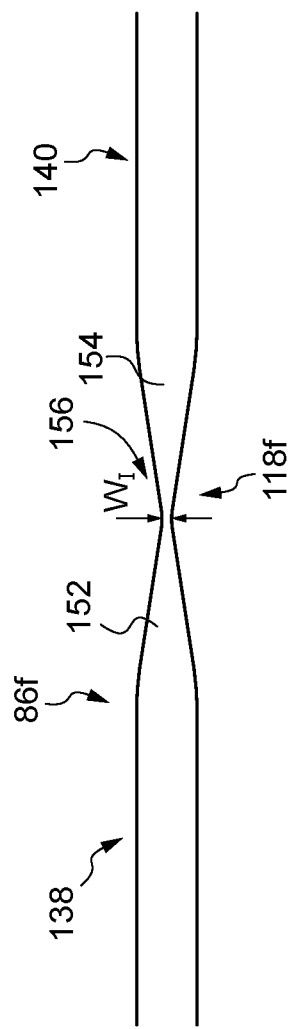
FIG. 24C is a side view of a variation on the liner shown in FIG. 24A.

In a variation on the liner 86f, which is shown in FIG. 24C, the portion 118f comprises the first transition section 152 extending from the first tendon sheath lining portion 138, and the second transition section 154 extending from the second tendon sheath lining portion 140, the second transition section being coupled to the first transition section. The transition sections 152 and 154 have a width which progressively increases from a width $W_I$ defined at an intersection 156 between the transition sections, to the width $W_{L2}$ of the respective tendon sheath lining portions 138 and 140.

The liner embodiment 86f shown in FIGS. 24A to C effectively comprises two tubular liners unitarily and symmetrically connected by two transition sections 152 and 154, reducing in width to form a section of uniform width 118f, similar to that of the pulling portion shown as 118 in FIG. 22 and FIGS. 23A and B. FIG. 24B shows how the liner 86f is coupled to the loop 96 connected to the threading element 26b. The liner 86f may be formed by removing material from the middle portion of a long tubular liner. Also, it is acceptable not to have the narrowed section of 118f shown in FIGS. 24A and B, but to include only the transition sections 152 and 154 as in FIG. 24C. This embodiment has two advantages: (i) simpler coupling and decoupling of the liner to the loop extending from the threading needle; and (ii) as two full length liners would be placed in the lumen of the tendon sheath, it would be possible to repair two ruptured tendons in the same finger (this occurs with some frequency), and in this case each liner would facilitate the delivery of one tendon stump at a time from the palm to the finger tip, again following the procedure that has been described elsewhere.

Figure 25:
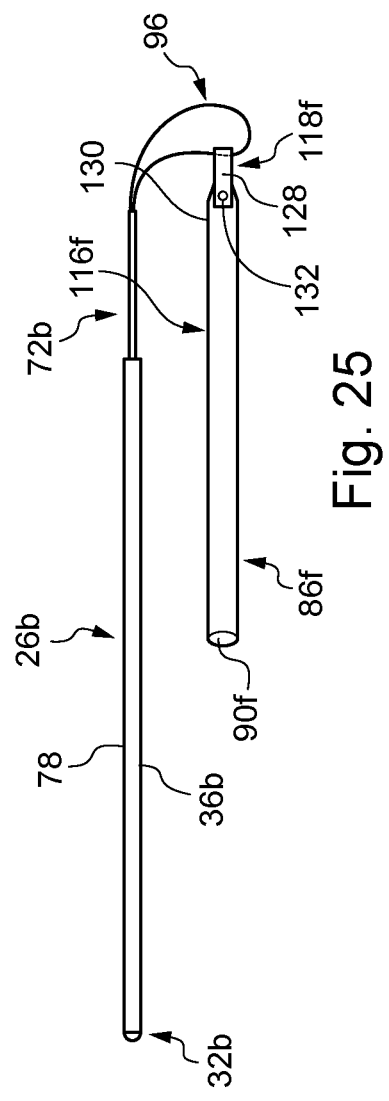
FIGS. 25 and 26 are side views of an assembly according to a further embodiment of the present disclosure, showing different features of the assembly.
Figure 26:
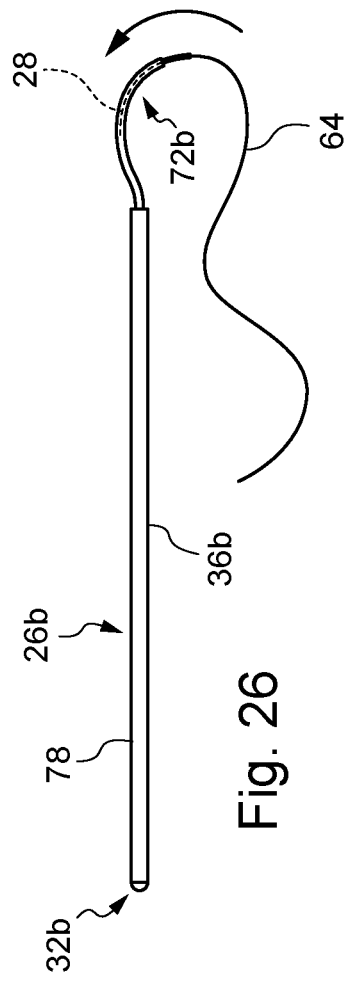

Turning now to FIGS. 25 and 26, there are shown side views of an assembly in accordance with another embodiment of the present disclosure. The assembly may be employed in a method of retrieving a tendon stump of a severed tendon, which involves lining the tendon sheath as a preparatory step to repairing the severed tendon. The assembly and method will be described with reference to the repair of a severed tendon in the hand, as described above.

In the illustrated embodiment, the assembly comprises a threading element 26b which is adapted to transit along a lumen 84 of the tendon sheath 20. The threading element 26b is provided by the needle covering and carrying device shown in FIG. 12 and described above, and so is indicated by the same reference numeral. It will be understood that further features of the threading element 26b are outlined above. Other threading elements may, however, be employed.

The assembly again comprises a liner for lining an internal surface 88 of the tendon sheath 20, the liner indicated generally by reference numeral 86f. Like components of the liner 86f with the liners 86 to 86e share the same reference numerals, with the suffix 'f'. The liner 86f defines an internal passage 90f along which a tendon stump can pass during transit along the lumen 84, and again acts to prevent contact between the tendon stump and the internal surface 88 of the tendon sheath 20.

The liner 86f is similar to the liners 86 to 86e shown in FIGS. 13 to 24 and described above, but is connected to the threading element 26b in a different way. Specifically, the liner 86f comprises a sheath lining portion 116f adapted to be located within the lumen 84 (for lining the tendon sheath 20), and a pulling portion 118f extending from the lumen lining portion. In this embodiment, the pulling portion 118f is folded over the loop formed by the suture 96, but is secured by fixing a folded part 128 of the pulling portion 118f to a main part 130 of the liner 86f, suitably by welding (e.g. application of heat) or using an adhesive, as shown at 132 in FIG. 25.

Figure 25A:
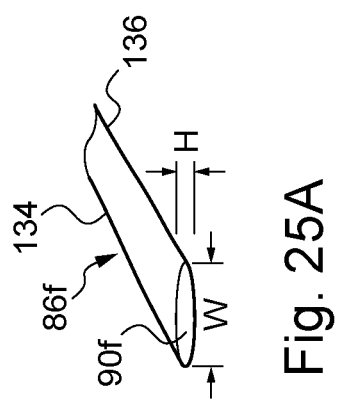
FIGS. 25A and 25B are enlarged perspective views of a liner forming part of the assembly shown in FIG. 25.
Figure 25B:
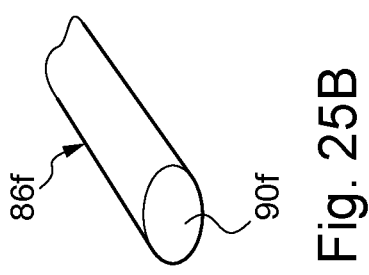

The liner 86f has a collapsed, rest configuration in which it is adapted to be inserted into the lumen of the tendon sheath, and an expanded, operating configuration. The liner 86f is shown in the collapsed, rest configuration in the perspective view of FIG. 25A, and in the expanded, operating configuration in FIG. 25B. The liner 86f is movable to the radially expanded configuration by contact with a tendon stump, in this case the first tendon stump 16 in the palm, as it moves along the lumen 84 of the tendon sheath 20.

In the collapsed configuration, the liner 86f is substantially flat (optionally taking the form of a lay-flat tube), having a width W and a height H, the width being greater than the height. During movement to the radially expanded configuration, the internal passage 90f defined by the liner 86f becomes enlarged or opens up, so that the liner becomes more rounded (circular or elliptical) in shape. This causes the width W to decrease and the height H to increase. This may be achieved by flattening the liner 86f, for example by winding it on to a reel prior to connecting it to the threading element 26b. This may cause the liner to have longitudinally extending seams or fold lines 134 and 136, spaced apart around a perimeter of the liner (although the seams may be deliberately formed, e.g. prior to winding on to a reel, if used), so that the liner looks like a flat tape when unreeled.

The 'lay-flat' structure of the liner 86f offers significant advantages over the dilation catheter disclosed in US-2013/0144310A1, in that avoids the over-dilation of tendon pulleys which can occur when using the rigid dilation catheter disclosed in the document, thereby reducing a risk of damage/rupture of the pulleys.

Typically, in particular embodiments, the liner 68f can have a wall thickness in the range of around 0.05 to around 0.2 mm, and so the height H in its collapsed (flat), rest configuration may be relatively small, for example, in the range of around 0.1 to around 0.4 mm (potentially up to around, for example, 0.5 mm depending upon how much the passage 90f is closed in the collapsed configuration). This ensures that the liner 86f occupies only a small portion of the lumen 84, and so does not interfere with or constrain transport of the tendon stump 16 along the lumen. In particular embodiments, the width W in comparison can be in the range of from about 5 to about 10 mm. Suitable materials for the liner 86f include polymeric materials, particularly low density polyethylene, which may be suitable for heat welding to connect it to the threading element 26b, and may facilitate flattening of the tube. In particular embodiments, a ratio of the height H to the width W can be in the range of from about 1:100 to about 1:10 (where W is from 5 to 10 mm and H is from 0.1 mm to 0.5 mm).

Forming the liner 86f so that it has a collapsed configuration can facilitate insertion of the liner into the lumen 84 of the tendon sheath 20, in that the height H is relatively small, and significantly smaller than the width W, when in this configuration. Subsequent movement of the liner 86f to the expanded configuration (as the tendon stump 16 passes along the internal passage 90f) enables passage of the stump 16 along the liner whilst ensuring that the liner does not come into contact with the pulleys or internal surface 88 of the tendon sheath 20, the liner therefore acting to line the internal surface.

FIG. 26 shows the assembly following disconnection of the liner 86f (which resides in the lumen 84 of the tendon sheath 20), and following location of the curved needle 28 within the portion 72b of the spring that forms the body 36b, trailing the suture 64. As shown, the first end 32*b* of the body 36*b* defined by the spring is rounded, to assist navigation along the lumen 84. This may be achieved by suitable treatment of the outer sleeve 78, for example the application of heat.

FIGS. 27 to 30 illustrate steps in a method of retrieving the tendon stump 16 from the palm 12 to a location proximate the second tendon stump 18 (not shown in these drawings) in the finger 18, employing the assembly of FIGS. 25 and 26. The method is similar to the relevant steps of the method shown in FIGS. 13 to 21 and described above.

FIG. 27 shows the assembly with the liner 86*f* connected to the threading element 26*b* via the suture 96, the threading element being used to draw the liner into the lumen 84 of the tendon sheath 20. FIG. 28 shows the liner 86*f* located in the lumen following disconnection of the liner from the threading element 26*b* (for example by cutting away the pulling portion 118*f* at a position spaced further along the liner from the welded/glued point 132 and then removing the suture 96 from the threading element), subsequent to connection of the suture 64 to the tendon stump using the curved needle 28, and subsequent to location of the needle 28 and the trailing end of the suture 64 within the internal cavity 38 (the tendon stump 16 is located behind the liner 86*f* in FIG. 28). FIG. 29 shows the threading element 26*b* inserted into and directed along the internal passage 90*f* defined by the liner 86 (located in the lumen 84 of the tendon sheath 20) trailing the tendon stump 16. FIG. 30 shows the tendon stump 16 being drawn along the internal passage 90*f* of the liner 86*f*, the threading element 26*b* having exited the aperture 70 in the finger 18. As will be understood from the foregoing description, the tendon stump 16 can then be sutured to the tendon stump 22 (not shown in these drawings) in the finger 18 to complete a repair procedure.

Various modifications may be made to the foregoing without departing from the spirit or scope of the present invention.

For example, the body may comprise a sidewall. An opening may be formed in the sidewall which communicates with the cavity. The needle may be insertable into the cavity through the opening.

The cavity may extend part way along a length of the body. The cavity may extend from one of the first and second ends in a direction towards the other one of the first and second ends. Where the second end is a trailing end, the cavity may extend from the second end towards the first end.

The device of the present invention has been shown during use in the repair of a damaged tendon in the hand (particularly, but not limited to, a severed tendon). It will be understood, however, that the device and method disclosed in this document may have a use in the repair of other tendons in the human or animal body. In general terms, the device and method may have a use in any surgical tendon repair technique which would benefit from the use of a curved needle to attach tendon stumps together and so repair the tendon, and which requires passage of the needle within a lumen of the tendon sheath.

The invention claimed is:

1. An assembly for use in repairing a severed tendon, the assembly comprising:
    a liner for lining an internal surface of a lumen of a tendon sheath, the liner defining an internal passage along which a tendon stump can pass during transit along the lumen, the liner acting to restrict contact between the tendon stump and the internal surface of the tendon sheath; and
    a threading element adapted to transit along and through the lumen of the tendon sheath;
    in which the liner is adapted to be releasably coupled to the threading element so that it can be drawn into the tendon sheath by the threading element and located within the lumen, and then released from the threading element so as to reside within the lumen, the threading element being configured to transit relative to and through the liner while the liner resides within the lumen of the tendon sheath.

2. An assembly as claimed in claim 1, in which the threading element serves for drawing the liner into the lumen of the tendon sheath, and can then be released from the liner so that the liner can be disposed within the lumen, in which position the liner serves to restrict contact between the tendon stump and the internal surface of the tendon sheath.

3. An assembly as claimed in claim 1, comprising a needle covering and carrying device for covering a curved needle and carrying the needle within the lumen of the tendon sheath, the needle covering and carrying device comprising an elongate element having:
    a first end;
    a second end opposite the first end; and
    a body extending between the first and second ends, the body defining an internal cavity for accommodating a curved needle so that at least a penetrating tip of the needle is disposed within the body, to protect the tendon sheath from damage through contact with the tip during passage of the needle within the sheath.

4. An assembly as claimed in claim 3, in which the body is at least partly deformable, and capable of being deformed into a curved shape so that it can accommodate the curved needle.

5. An assembly as claimed in claim 4, in which the body forms the threading element, the body comprising a portion defining the threading element and a portion which forms a cover for the needle.

6. An assembly as claimed in claim 5, wherein the portion of the body that forms the threading element is straight and has a first length, the portion of the body that forms the cover for the needle has a second length, which is less than the first length.

7. An assembly as claimed claim 6, wherein the portion of the body that forms the cover for the needle is configured to elastically deform from a non-deformed state into a deformed state having the curved shape upon insertion of the needle through an open end of the cover into the internal cavity.

8. An assembly as claimed in claim 1, in which the liner comprises an outer surface adapted to contact the internal surface of the tendon sheath, and an inner surface which defines the internal passage.

9. An assembly as claimed in claim 1, in which the liner comprises a first axial end and a second axial end, and a slit extending along a length of the liner from the first axial end to the second axial end, to facilitate removal of the liner from the lumen following completion of a tendon repair procedure.

10. An assembly as claimed in claim 1, in which the liner comprises a sheath lining portion adapted to be located within the lumen of the tendon sheath, and a pulling portion extending from the sheath lining portion and adapted to be used to pull the sheath lining portion into and along the lumen.

11. An assembly as claimed in claim 10, in which the threading element is adapted to be coupled to the pulling portion, and used to draw the pulling portion into the lumen.

12. An assembly as claimed in claim 10, in which the pulling portion is adapted to be gripped by a user to pull the sheath lining portion into the lumen.

13. An assembly as claimed in claim 10, in which the sheath lining portion is substantially tubular and the pulling portion comprises one or more elongate legs which extend from the substantially tubular sheath lining portion.

14. An assembly as claimed in claim 1, in which the threading element takes the form of a spring, and the threading element further comprises an outer sheath having an inner surface which is disposed in contact with an outer surface of the spring.

15. An assembly as claimed in claim 1, comprising a flexible connecting component for releasably connecting the threading element to the liner.

16. An assembly as claimed in claim 15, in which the flexible connecting component comprises a loop, and the liner is folded over a portion of the loop.

17. An assembly as claimed in claim 1, in which the liner is coupled to the threading element so as to define two tendon sheath lining portions, a first tendon sheath lining portion serving for receiving the tendon stump, a second tendon sheath lining portion serving for receiving a second tendon stump.

18. An assembly as claimed in claim 17, in which the liner has a first end and a second end, and is coupled to the threading element at a point along a length of the liner between the first and second ends.

19. An assembly as claimed in claim 18, in which the first tendon sheath lining portion extends from the first end towards a part of the liner disposed between the first and second ends, and the second tendon sheath lining portion extends from the second end towards the part disposed between the first and second ends.

20. An assembly as claimed in claim 19, in which the first and second tendon sheath lining portions each have a width, and the part disposed between the ends has a width which is less than the width of the first and second tendon sheath lining portions.

21. An assembly as claimed in claim 19, in which said part of the liner comprises: a main section of substantially constant width; a first transition section extending between the main section and the first tendon sheath lining portion; and a second transition section extending between the main section and the second tendon sheath lining portion.

22. An assembly as claimed in claim 21, in which the transition sections each have a width which progressively increases from the width of the main section to the width of the respective tendon sheath lining portion.

23. An assembly as claimed in claim 19, in which said part of the liner comprises: a first transition section extending from the first tendon sheath lining portion; and a second transition section extending from the second tendon sheath lining portion and coupled to the first transition section; and in which the transition sections each have a width which progressively increases from a width defined by an intersection between the transition sections, to the width of the respective tendon sheath lining portions.

24. An assembly as claimed in claim 1, wherein the liner is configured to line an entirety of the lumen of the tendon sheath from a first aperture in the tendon sheath to a second aperture in the tendon sheath.

25. An assembly as claimed in claim 1, wherein the liner is configured to collapse into a flattened state having first and second longitudinally extending fold lines extending along a length of the liner.

26. An assembly as claimed in claim 1, wherein the liner is made of polyethylene.

27. An assembly for use in repairing a severed tendon, the assembly comprising:
a threading element adapted to transit along a lumen of a tendon sheath; and
a liner for lining an internal surface of the tendon sheath, the liner defining an internal passage along which a tendon stump can pass during transit along the lumen, the liner acting to restrict contact between the tendon stump and the internal surface of the tendon sheath;
in which the liner is adapted to be releasably coupled to the threading element so that it can be drawn into the tendon sheath by the threading element and located within the lumen, and then released from the threading element so as to reside within the lumen;
wherein the threading element comprises a body having an internal cavity for accommodating a curved needle and in which the body comprises a deformable portion configured to deform into a curved shape so that it can accommodate the curved needle upon insertion of the needle into the internal cavity of the body.

28. An assembly as claimed in claim 27, wherein the threading element comprises a loop element that releasably couples the liner to the threading element.

29. An assembly as claimed in claim 28, wherein the loop element comprises a wire.

30. An assembly as claimed in claim 27, wherein the deformable portion of the body is configured to elastically deform from a non-deformed state into a deformed state having the curved shape upon insertion of the needle through an open end of the body into the internal cavity.

31. An assembly as claimed in claim 30, wherein the deformable portion of the body is straight in the non-deformed state.

32. An assembly as claimed in claim 31, wherein the deformable portion of the body comprises a helical coil.

33. An assembly as claimed in claim 30, wherein the deformable portion of the body is a first portion of the body and the body comprises a second portion extending from the first portion, wherein the second portion is less flexible than the first portion.

34. An assembly as claimed in claim 30, wherein the deformable portion of the body is a first portion of the body and the body comprises a second portion extending from the first portion, wherein the first portion has a first length and the second portion has a second length that is greater than the first length.

35. An assembly as claimed in claim 34, wherein the second portion is straight.

36. An assembly as claimed in claim 27, wherein the liner is made of polyethylene.

37. An assembly as claimed in claim 27, wherein the liner is configured to collapse into a flattened state having first and second longitudinally extending fold lines extending along a length of the liner.

38. An assembly as claimed in claim 27, wherein the liner is configured to line an entirety of the lumen of the tendon sheath from a first aperture in the tendon sheath to a second aperture in the tendon sheath.

* * * * *